United States Patent
Chin

(10) Patent No.: US 11,992,687 B2
(45) Date of Patent: May 28, 2024

(54) SYSTEM AND METHOD FOR RATE MODULATED CARDIAC THERAPY UTILIZING A TEMPERATURE SENSOR

(71) Applicant: Pacesetter, Inc., Sylmar, CA (US)

(72) Inventor: Donald Chin, Palo Alto, CA (US)

(73) Assignee: Pacesetter, Inc., Sylmar, CA (US)

( * ) Notice: Subject to any disclaimer, the term of this patent is extended or adjusted under 35 U.S.C. 154(b) by 449 days.

(21) Appl. No.: 17/393,634

(22) Filed: Aug. 4, 2021

(65) Prior Publication Data

US 2021/0361945 A1 Nov. 25, 2021

Related U.S. Application Data

(63) Continuation of application No. PCT/US2020/023520, filed on Mar. 19, 2020.

(60) Provisional application No. 62/822,295, filed on Mar. 22, 2019.

(51) Int. Cl.
*A61N 1/365* (2006.01)
*A61N 1/37* (2006.01)

(52) U.S. Cl.
CPC .......... *A61N 1/3655* (2013.01); *A61N 1/3704* (2013.01)

(58) Field of Classification Search
CPC ... A61N 1/3655; A61N 1/3704; A61N 1/3756
See application file for complete search history.

(56) References Cited

U.S. PATENT DOCUMENTS

| 3,867,950 A | 2/1975 | Fischell |
| 4,436,092 A | 3/1984 | Cook et al. |
| 4,543,954 A | 10/1985 | Cook et al. |
| 4,688,573 A | 8/1987 | Alt |
| 4,803,987 A | 2/1989 | Calfee et al. |
| 5,005,574 A | 4/1991 | Fearnot et al. |

(Continued)

FOREIGN PATENT DOCUMENTS

| CN | 106924877 A | 7/2017 |
| EP | 0256617 A2 | 2/1988 |

OTHER PUBLICATIONS

Response to Communication pursuant to Rules 161(1) and 162(EPC) dated Jan. 24, 2022, European Patent Application No. 20719830.0.

(Continued)

*Primary Examiner* — Mallika D Fairchild
(74) *Attorney, Agent, or Firm* — Vierra Magen Marcus LLP

(57) ABSTRACT

Described herein are implantable medical systems, and methods for use therewith, that provide a temperature based rate response for a patient within which the implantable medical system is implanted. Such a method can include sensing a blood temperature signal indicative of a core body temperature of the patient, and producing a relative temperature signal based on the blood temperature signal. The method can further include producing a moving baseline temperature signal based on the relative temperature signal, producing a proportional response signal based on the relative temperature signal and the moving baseline temperature signal, and producing a sensor indicated rate response signal based on the proportional response signal and a base rate. The sensor indicated rate response signal can also be based on a dip response signal and/or a slope response signal. Additionally, a pacing rate is controlled based on the sensor indicated rate response signal.

24 Claims, 12 Drawing Sheets

(56) References Cited

U.S. PATENT DOCUMENTS

| | | | |
|---|---|---|---|
| 7,142,920 B2 | 11/2006 | Scheiner et al. |
| 7,925,343 B1 | 4/2011 | Min et al. |
| 7,937,148 B2 | 5/2011 | Jacobson |
| 8,543,205 B2 | 9/2013 | Ostroff |
| 8,573,062 B2 | 11/2013 | Zhao et al. |
| 9,833,624 B2 | 12/2017 | Chin et al. |
| 10,159,841 B2 | 12/2018 | Chin et al. |
| 2012/0109236 A1 | 5/2012 | Jacobson et al. |
| 2013/0261497 A1 | 10/2013 | Pertijs et al. |
| 2015/0328459 A1 | 11/2015 | Chin et al. |
| 2018/0126161 A1 | 5/2018 | Chin et al. |

OTHER PUBLICATIONS

Notice of Allowance dated Aug. 22, 2017, U.S. Appl. No. 14/712,499, filed May 14, 2015.
Amendment filed Jul. 17, 2017, U.S. Appl. No. 14/712,499, filed May 14, 2015.
Non-final Office Action dated Jun. 30, 2017, U.S. Appl. No. 14/712,499, filed May 14, 2015.
International Search Report & The Written Opinion of the International Searching Authority dated Jun. 24, 2020, International Application No. PCT/US2020/023520.
Communication under Rule 71(3) EPC dated Mar. 16, 2023, European Patent Application No. 20719830.0.
Office Action dated Jan. 4, 2024, Chinese Patent Application No. 202080023170.5.
English Abstract of Chinese Publication No. CN106924877 published Jul. 7, 2017.

SYSTEM AND METHOD FOR RATE MODULATED CARDIAC THERAPY UTILIZING A TEMPERATURE SENSOR

PRIORITY CLAIM

The present application is a continuation of International Application No. PCT/US2020/023520, filed Mar. 19, 2020, which claims priority to U.S. Provisional Patent Application No. 62/822,295, filed Mar. 22, 2019. Priority is claimed to each of the above applications, each of which is incorporated herein by reference.

RELATED PATENTS

The present application is related to commonly assigned U.S. Pat. Nos. 9,833,624 and 10,159,841, both of which are titled SYSTEM AND METHOD FOR RATE MODULATED CARDIAC THERAPY UTILIZING A TEMPERATURE SENOR.

FIELD

This disclosure is directed to medical devices and methods for cardiac rhythm management. More specifically, embodiments disclosed herein relate to systems and methods for automatically adjusting the operating parameters of a cardiac rhythm management system.

BACKGROUND

The normal human heart supplies oxygen and removes waste products by providing a demand-based supply of blood to all tissues of the body. The volume of blood that is pumped through the body is determined by the person's heart rate and stroke volume. The heart beats approximately 60 beats per minute (bpm) in a normal healthy resting individual and is regulated through a complex autonomic control mechanism which governs that the rate the sinoatrial (SA) node fires. The SA node controls heart rate. As an individual does work, there is increased metabolic demand on tissues and the autonomic control system responds by causing the SA node to fire more rapidly, thereby increasing heart rate. In a healthy individual, interaction of the nervous system, SA node, and heart rate assures that a balance is maintained throughout all levels of activity.

Most modern pacemakers have the ability to approximate the body's changing needs based on activity through the use of an electrical component called an accelerometer. For example, many pacemakers include an accelerometer that can detect motion (and more specifically, acceleration) as a proxy for activity. Changes in the motion as a person walks, runs, or does other activities send signals to the pacemaker's internal electronics to cause the pacemaker to increase heart rate to provide an active person with increased blood supply. A limitation of depending on an accelerometer to adjust pacing rate is that an accelerometer can interpret any motion as patient activity, such as riding in a car or on a bicycle down a bumpy road, which may result in a pacemaker inappropriately increasing a pacing rate. In other words, an accelerometer can mistakenly interpret certain increases in motion as increases in patient activity, even though such increases in motion are not actually due to increases in patient activity. Another limitation of depending on an accelerometer to adjust a pacing rate is that an accelerometer can, in certain instances, fail to detect increases in patient activity that are not accompanied by device vibration, such as when an individual rides a stationary bike while keeping their upper body relatively still. Either situation can cause a pacemaker to misinterpret activity and deliver inappropriate pacing rate control.

An alternative means of controlling the rate of a pacemaker is through the use of a blood temperature sensor. A rise in a person's core body temperature (often first preceded by a small dip in the core body temperature) is typically observed at the onset of activity and can be used as an alternative to an accelerometer. However, current pacemakers that rely on a person's core body temperature to adjust a pacing rate sometimes do not appropriately and/or sufficiently respond to changes in a person's activity level.

SUMMARY OF THE DISCLOSURE

A summary of several sample aspects of the disclosure follows. It should be appreciated that this summary is provided for the convenience of the reader and does not wholly define the breadth of the disclosure. For convenience, one or more aspects or embodiments of the disclosure may be referred to herein simply as "some aspects" or "certain embodiments."

In general, the disclosure is directed to a cardiac rhythm management system, and methods for use therewith, that provides an appropriate and proportional increase in pacing rate in response to exercise, based on measurements of blood temperature.

Certain embodiments of the present technology are related to implantable medical systems, and methods for use therewith, that provide a temperature based rate response for a patient within which the implantable medical system is implanted. Such an implantable medical system can include a single implantable medical device (IMD), or multiple IMDs that may communicate with one another. Such a method can include sensing a blood temperature signal indicative of a core body temperature of the patient within which the IMD is implanted, and producing a relative temperature signal based on the blood temperature signal. In accordance with certain embodiments, the relative temperature signal can be produced by producing a short term average (STA) of the blood temperature signal, producing a long term average (LTA) of the blood temperature signal, and subtracting the LTA of the blood temperature signal from the STA of the blood temperature signal to thereby produce the relative temperature signal. The method can further include producing a moving baseline temperature signal based on the relative temperature signal, producing a proportional response signal based on the relative temperature signal and the moving baseline temperature signal, and producing a sensor indicated rate response signal based on the proportional response signal and a base rate. Additionally, the method can include controlling a pacing rate of the implantable medical system based on the sensor indicated rate response signal.

In accordance with certain embodiments, the moving baseline temperature signal is produced based on the relative temperature signal by producing the moving baseline temperature signal such that it follows the relative temperature signal during an initial drop in the blood temperature signal that occurs during an onset of activity, and decays towards zero during an upswing in the blood temperature signal that follows the initial drop in the blood temperature signal. The proportional response signal can, for example, be produced by subtracting the moving baseline temperature signal from the relative temperature signal to produce a difference signal indicative of a difference between the relative temperature signal and the moving baseline temperature signal, and the proportional response signal can be produced based on positive portions of the difference signal. For example, positive portions of the difference signal can be multiplied by a proportional gain value to thereby produce the proportional response signal. Alternatively, a predetermined function can be applied to positive portions of the difference signal to thereby produce the proportional response signal. The proportional response signal can provide for an increase in the pacing rate, based on a difference between the relative temperature signal and the moving baseline temperature signal, during an upswing in the blood temperature signal that follows an initial drop in the blood temperature signal that occurs during an onset of activity. Additionally, the proportional response can provide for a decrease in the pacing rate, based on the difference between the relative temperature signal and the moving baseline temperature signal, during a downswing in the blood temperature signal that occurs in response to a reduction or cessation in activity.

In accordance with certain embodiments, a dip response signal and/or a slope response signal can also be produced and used to produce the sensor indicated rate response signal. The dip response signal can provide for an increase in the pacing rate during an initial drop in the blood temperature signal that occurs during an onset of activity. The slope response signal can provide for an increase in the pacing rate, based on a slope of the relative temperature signal, during an upswing in the blood temperature signal that follows an initial drop in the blood temperature signal. In certain embodiments, the sensor indicated rate response signal is produced based on a combination of the proportional response signal, the dip response signal, the slope response signal, and the base rate. For example, the sensor indicated rate response signal can be produced by summing the proportional response signal, the dip response signal, the slope response signal, and the base rate. In accordance with certain embodiments, a magnitude and/or a slew rate of the sensor indicated rate response signal is/are limited to prevent the pacing rate from exceeding a maximum rate and/or preventing a change in the pacing rate from exceeding a maximum rate of change.

In accordance with certain embodiments, the dip response signal can be produced by comparing the relative temperature signal to a dip threshold, providing a dip onset rate value to an input of an integrator while the relative temperature signal is less than the dip threshold, providing a dip decay rate value to the input of the integrator while the relative temperature signal is greater than the dip threshold, and using positive portions of a signal output by the integrator as the dip response signal.

In accordance with certain embodiments, the slope response signal can be produced by producing a signal indicative of a positive slope of the relative temperature signal, and either multiplying the signal indicative of the positive slope of the relative temperature signal by a slope gain value to thereby produce the slope response signal, or applying a predetermined function to the signal indicative of the positive slope of the relative temperature signal to thereby produce the slope response signal. In accordance with certain embodiments, the signal indicative of the positive slope of the relative temperature signal can be produced by providing the relative temperature signal to a high pass filter (HPF), and providing an output of the HPF to a rectifier to thereby produce the signal indicative of the positive slope of the relative temperature signal. Alternatively, a difference between two temporally different samples of the relative temperature signal can be determined, and the signal indicative of the positive slope of the relative temperature signal can be determined based on the difference.

In accordance with certain embodiments, an implantable medical system includes, inter alia, one or more pulse generators, one or more electrodes, a temperature sensor, and a controller. The pulse generator(s) is/are configured to selectively produce pacing pulses. The electrode(s) is/are configured to deliver pacing pulses produced by the pulse generator(s) to a heart of a patient within which the implantable medical system is implanted. The temperature sensor is configured to produce a blood temperature signal indicative of a core body temperature of the patient within which the implantable medical system is implanted. The controller is to produce a relative temperature signal based on the blood temperature signal, produce a moving baseline temperature signal based on the relative temperature signal, and produce a proportional response signal based on the relative temperature signal and the moving baseline temperature signal. The controller is also configured to produce a sensor indicated rate response signal based on the proportional response signal and a base rate, and control delivery of the pacing pulses to thereby control a pacing rate based on the sensor indicated rate response signal. The controller can also be configured to produce a dip response signal and/or a slope response signal, and produce the sensor indicated rate response signal also based the dip response signal and/or the slope response signal. The dip response signal provides for an increase in the pacing rate during an initial drop in the blood temperature signal that occurs during an onset of activity. The slope response signal provides for an increase in the pacing rate, based on a slope of the relative temperature signal, during an upswing in the blood temperature signal that follows an initial drop in the blood temperature signal. In specific embodiments, the controller produces the sensor indicated rate response signal based on a combination of the proportional response signal, the dip response signal, the slope response signal, and the base rate.

This summary is not intended to be a complete description of, or limit the scope of, the present technology. Alternative and additional features, aspects, and objects of the present technology can be obtained from a review of the specification, the figures, and the claims.

BRIEF DESCRIPTION OF THE DRAWINGS

The novel features of the present technology are set forth with particularity in the claims that follow. A better understanding of the features and advantages of the present technology will be obtained by reference to the following detailed description that sets forth illustrative embodiments, in which the principles of the present technology are utilized, and the accompanying drawings of which:

Figure 1A:
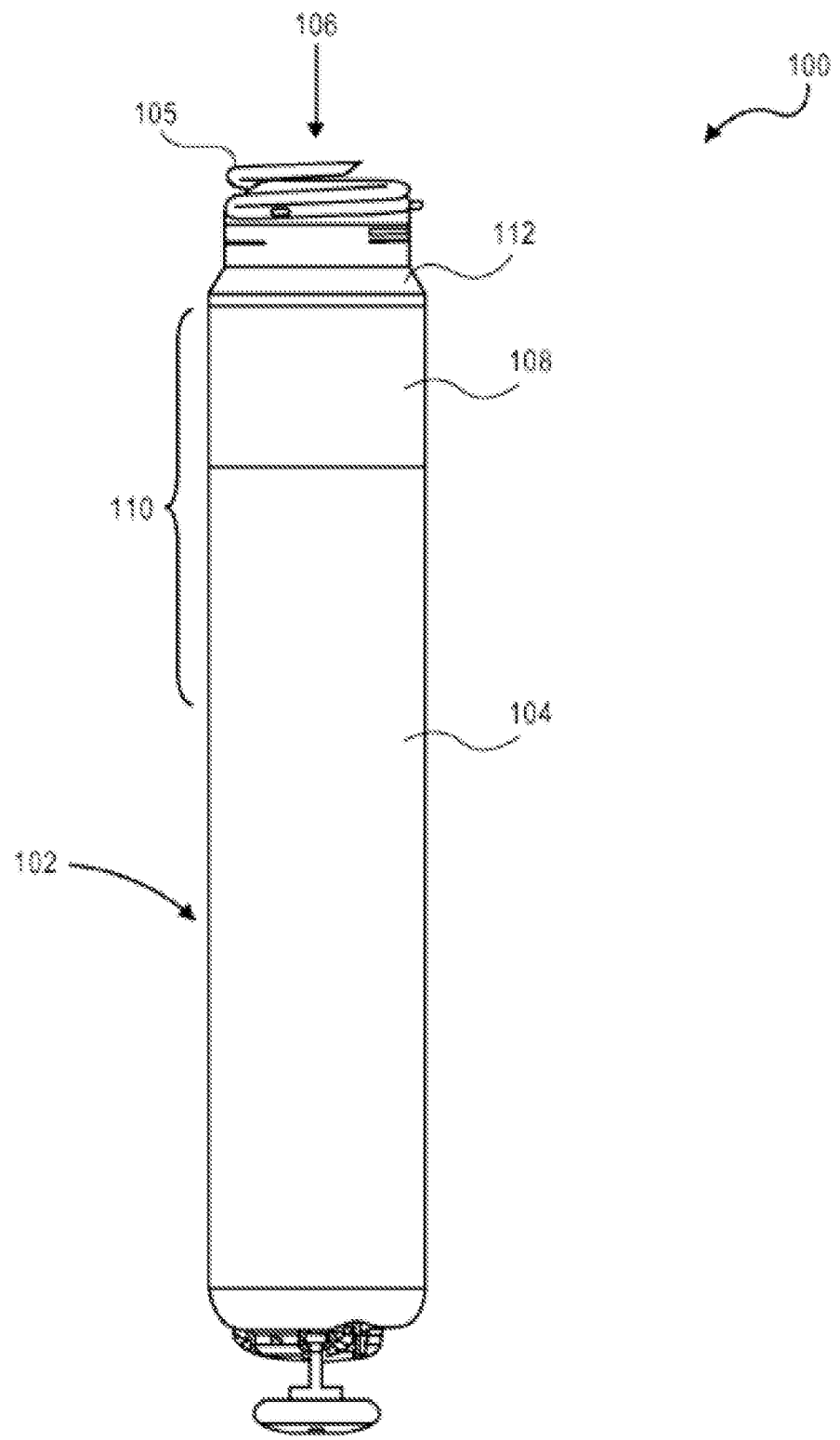
FIG. 1A is a simplified diagram of an embodiment of a leadless cardiac pacemaker.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

Embodiments of the present technology are described below, with reference to detailed illustrative embodiments. It will be apparent that the embodiments described herein may be embodied in a wide variety of forms, some of which may appear to be quite different from those of the disclosed embodiments. Consequently, the specific structural and functional details disclosed herein are merely representative and do not limit the scope of the present technology. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

This disclosure relates to cardiac rhythm management systems responsive to temperature. The cardiac rhythm management systems may include one or more implantable medical devices, including, but not limited to: a leadless cardiac pacemaker that can be implanted within a chamber of the patient's heart; an intra-cardiac implantable medical devices that utilizes an IC device extension to afford dual chamber functionality; a cardiac pacemaker and/or implantable cardioverter-defibrillator (ICD) that utilizes one or more electrically-conductive leads that traverses blood vessels and heart chambers in order to connect a canister with electronics and a power source (the can) to electrodes affixed to the heart for the purpose of electrically exciting cardiac tissue and measuring myocardial electrical activity; a subcutaneous ICD that does not use endocardial, transvenous, or epicardial lead wires to deliver defibrillation (but may employ an endocardial, transvenous, or epicardial lead wire to sense temperature) and can deliver defibrillation using subcutaneous electrodes; a temperature sensor implanted into a heart or associated blood vessels of a patient; an intracardiac monitor that includes a temperature sensor, which may be a stand-alone device or part of a lead; a master device, programmer, or an implantable cardiac monitor that does not pace the heart itself, which may contain a processor that analyzes temperatures and provides a sensor indicated rate and is in communication with another implantable medical device of the cardiac rhythm management system.

In certain embodiments, the temperature sensor and/or processor that analyzes temperatures and provides a sensor indicated rate could be employed in a micro-mechanical system ("MEMS"), such as described, e.g., in U.S. Pat. No. 8,573,062. The MEMS can be a stand-alone device, which in some embodiments is implanted on the epicardium of the heart or into a cardiac chamber using, for example, a helix and sutures employed to affix the device directly to cardiac muscle, as described, e.g., in U.S. Pat. No. 7,937,148. In embodiments not including the temperature sensor, the MEMS stand-alone device can be implanted in other locations of the body. The MEMS can be configured to communicate with a stimulation device through wireless communication, for example through conductive communication as described in U.S. Pat. No. 9,168,383, by for example incorporating a communication pulse generator. In alternative embodiments, the MEMS is incorporated into an implantable lead and may communicate with the stimulation device through wired communication.

Some embodiments of a leadless cardiac pacemaker may include a hermetic housing disposed in a chamber of a human heart, a battery disposed in the housing, at least two electrodes supported by the housing, a temperature sensor enclosed or contained within the housing and a controller disposed in the housing. The controller can be adapted to sense intracardiac information using the two electrodes and to deliver stimulation energy from the battery to the electrode using temperature information from the temperature sensor. The temperature sensor may be a thermistor or a semiconductor temperature sensor incorporated into the controller.

FIG. 1A shows an external view of a leadless pacemaker or biostimulator 100. Biostimulator 100 can include a hermetic housing 102 with electrodes 104 and 106 located within, on, or near the housing 102, for delivering pacing pulses to and sensing electrical activity from the muscle of the cardiac chamber, and for bidirectional communication with at least one other device within or outside the body. In various embodiments, the electrodes 104 and 106 can be coupled on, within, or within two centimeters of the housing 102. In alternative embodiments, the electrodes 104 and 106 can be coupled on, within, or within fifteen centimeters of the housing 102. In some arrangements, the electrodes 104 and 106 can be formed integrally to an outer surface of the housing 102.

As shown, electrode 106 can be separated from but surrounded partially by a fixation mechanism 105, and the electrode 104 can be disposed on the housing 102. The fixation mechanism 105 can be a fixation helix, a plurality of hooks, barbs, or other attaching features configured to attach the pacemaker to tissue, such as heart tissue.

The housing can also include an electronics compartment 110 within the housing that contains the electronic components necessary for operation of the pacemaker, including, for example, a pulse generator, communication electronics, a battery, and a processor for operation. The hermetic housing 102 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 104 and 106. The insulator can be an insulative coating on a portion of the housing between the electrodes, and can comprise materials such as silicone, polyurethane, parylene, or another biocompatible electrical insulator commonly used for implantable medical devices. In the embodiment of FIG. 1A, a single insulator 108 is disposed along the portion of the housing between electrodes 104 and 106. In some embodiments, the housing itself can comprise an insulator instead of a conductor, such as an alumina ceramic or other similar materials, and the electrodes can be disposed upon the housing.

As shown in FIG. 1A, the pacemaker can further include a header assembly 112 to isolate electrode 104 from electrode 106. The header assembly 112 can be made from PEEK, tecothane or another biocompatible plastic, and can contain a ceramic to metal feedthrough, a glass to metal feedthrough, or other appropriate feedthrough insulator as known in the art.

The electrodes 104 and 106 can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 1A, electrode 106 can be a pace/sense electrode and electrode 104 can be a return electrode. The electrode 104 can be a portion of the conductive housing 102 that does not include an insulator 108.

Several techniques and structures can be used for attaching the housing 102 to the interior or exterior wall of the heart. A helical fixation mechanism 105, can enable insertion of the device endocardially or epicardially through a guiding catheter. A torqueable catheter can be used to rotate the housing and force the fixation device into heart tissue, thus affixing the fixation device (and also the electrode 106 in FIG. 1A) into contact with stimulable tissue. Electrode 104 can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 1B:
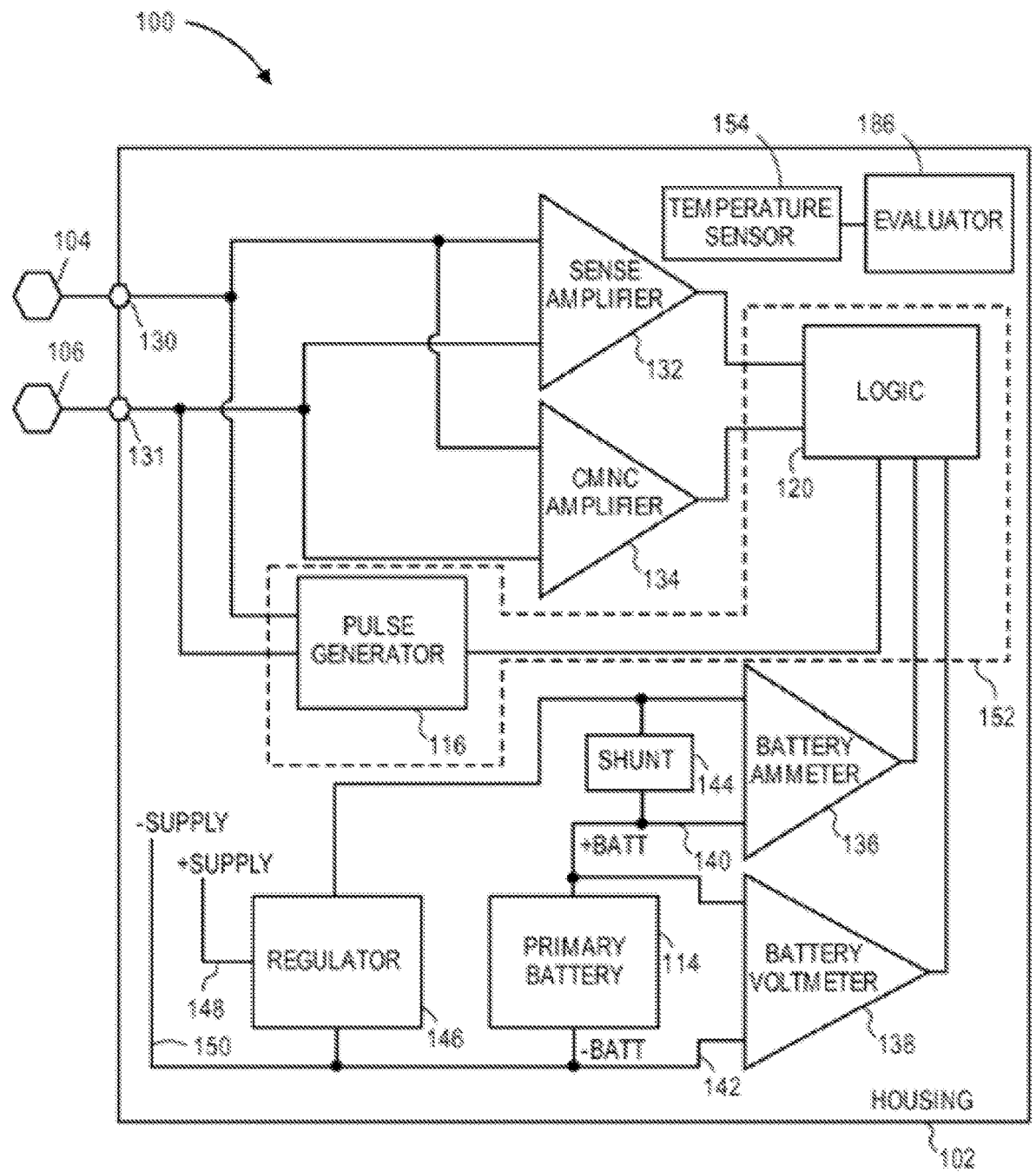
FIG. 1B is a schematic block diagram showing interconnection of operating elements of an embodiment of the illustrative rate-responsive leadless cardiac pacemaker.

Turning to FIG. 1B, a schematic block diagram depicts an embodiment of biostimulator 100. The biostimulator 100 comprises a housing 102, electrodes 104 and 106 coupled to the housing 102, a pulse delivery system 152 hermetically contained within the housing 102 and electrically coupled to the electrodes 104 and 106. The pulse delivery system 152 configured for sourcing energy internal to the housing 102, generating and delivering electrical pulses to the electrodes 104 and 106. The biostimulator 100 further comprises a temperature sensor 154 which may be enclosed within the housing 102 or may be supported by the housing 102 and adapted to sense temperature. A logic 120, for example a processor, controller, central processing unit, state machine, programmable logic array, and the like, is hermetically contained within the housing 102 and communicatively coupled to the pulse generator 116, the temperature sensor 154, and the electrodes 104 and 106. Logic 120 may control pulse generator 116 to deliver electrical pulses with the amplitudes, pulse widths, frequency, or electrode polarities specified by selected one or more therapy programs stored in a memory. Temperature sensor 154 is connected to evaluator 186. Exemplary embodiments of the temperature sensor 154 are discussed below with reference to FIGS. 2A, 2B and 2C. However, other types of temperature sensors can alternatively be used. The evaluator 186 is used to provide a sensor indicated rate for pacing a heart according to certain embodiments of the disclosure. The evaluator 186 is connected to the logic 120. The sensor indicated rate output of evaluator 186 is used by logic 120 to generate control signals specifying stimulation therapy, such as pacing rate, sent to pulse generator 116.

The logic 120 and other blocks can be implemented by software, firmware, or combinations thereof. A software module may reside in RAM memory, flash memory, ROM memory, EPROM memory, EEPROM memory, registers, or any other form of storage medium known in the art. An exemplary storage medium is coupled to the processor such the processor can read information from, and write information to, the storage medium. In the alternative, the storage medium may be integral to the processor. In certain embodiments, the logic 120 comprises an application-specific integrated circuit (ASIC) and the temperature sensor 154 comprises a semiconductor temperature sensor incorporated into the ASIC. The evaluator 186 and storage medium may reside in the ASIC. In certain embodiments, logic 120 can comprise a single ultra-low power ASIC chip configured to sense, pace, and communicate. The logic 120 can control electrical pulse delivery at least partly based on the output of evaluator 186.

In some embodiments, the logic 120 can be a processor that controls electrical pulse delivery and application of the temperature sensor 154 and evaluator 186 according to one or more programmable parameters with the processor programmable by communication signals transmitted via the electrodes 104 and 106. The information communicated on the incoming communication channel can include, but is not limited to pacing rate, pulse duration, sensing threshold, and other parameters commonly programmed externally in typical pacemakers, as well as a temperature signal generated by an external temperature sensor. The information communicated on the outgoing communication channel can include, but is not limited to programmable parameter settings, event counts (pacing and sensing), battery voltage, battery current, and other information commonly displayed by external programmers used with common pacemakers, as well as a temperature signal. The outgoing communication channel can also echo information from the incoming channel, to confirm correct programming. The logic 120 and the evaluator 186, alone or in combination, can be referred to as a controller. Such a controller can include one or more processor, software, firmware, hardware, or a combination thereof.

Hermetic feedthroughs 130, 131 conduct electrode signals through the housing 102. The housing 102 contains a primary battery 114 to provide power for pacing, sensing, and communication. The housing 102 contains circuits 132 for sensing cardiac activity from the electrodes 104 and 106; circuits 134 for receiving information from at least one other device via the electrodes 104 and 106; and a pulse generator 116 for generating pacing pulses for delivery via the electrodes 104 and 106 and also for transmitting information to at least one other device via the electrodes 104 and 106. The pacemaker 100 further contains circuits for monitoring device health, for example a battery current monitor 136 and a battery voltage monitor 138. Logic 120 controls these operations in a predetermined manner.

The primary battery 114 has positive terminal 140 and negative terminal 142. In certain embodiments, the battery is a lithium carbon monofluoride (Li/CFx) battery. Current from the positive terminal 140 of primary battery 114 flows through a shunt 144 to a regulator circuit 146 to create a positive voltage supply 148 suitable for powering the remaining circuitry of the pacemaker 100. The shunt 144 enables the battery current monitor 136 to provide the logic 120 with an indication of battery current drain and indirectly of device health.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Figure 2A:
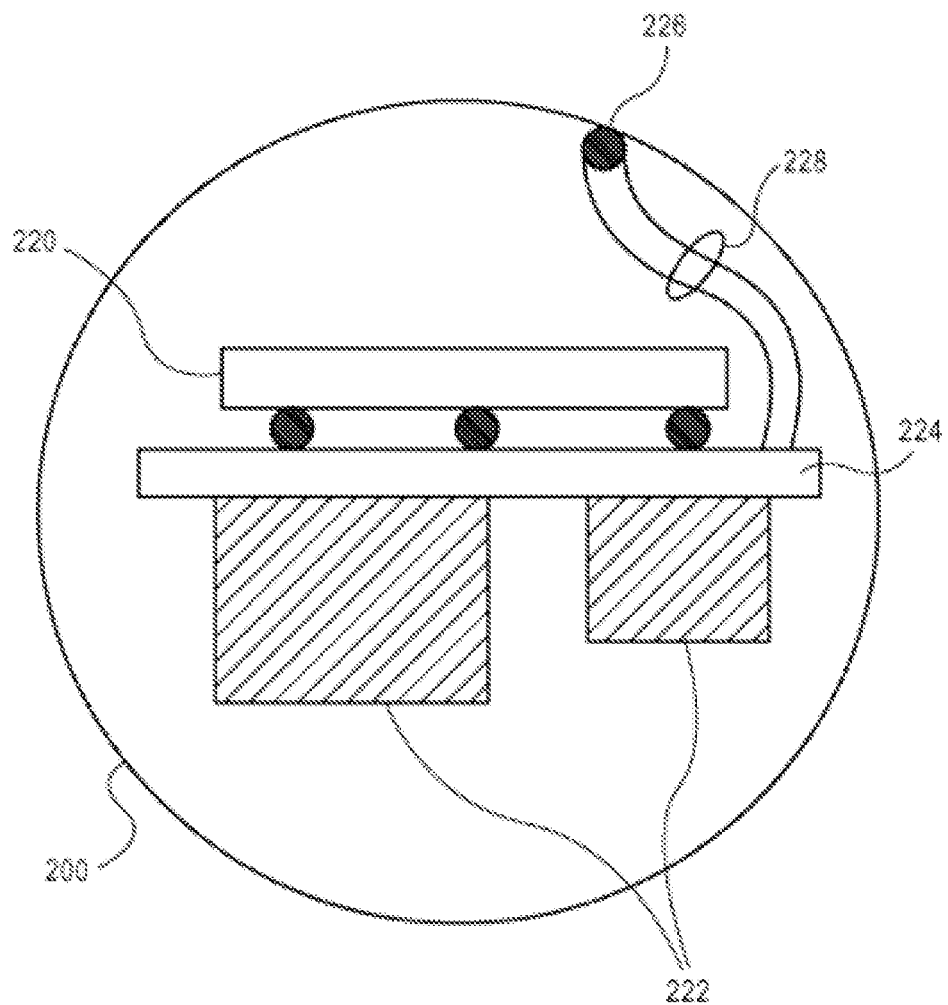
FIGS. 2A, B, and C illustrate three embodiments of a temperature sensor in a leadless cardiac pacemaker.

In the embodiment of FIG. 2A, the temperature sensor (e.g., 154 in FIG. 1B) can be a thermistor 226 disposed within a housing 200. As shown in this cross-sectional view, thermistor 226 can be bonded so as to be thermally connected to an inside surface of housing 200, and the thermistors can connect to ASIC controller 220 via leads 228 and substrate 224. Thus, thermistor 226 can be configured to sense the temperature of blood surrounding the biostimulator through housing 200. Other elements within housing 200 include the ASIC substrate 224, other electronic components 222, and a battery (not shown). At least two electrodes can be supported by, and exterior to, the housing. In some embodiments, the ASIC 220 can be adapted to sense intracardiac information using the electrodes and to deliver stimulation energy from the battery to one of the electrodes using temperature information from the thermistor 226.

Figure 2B:
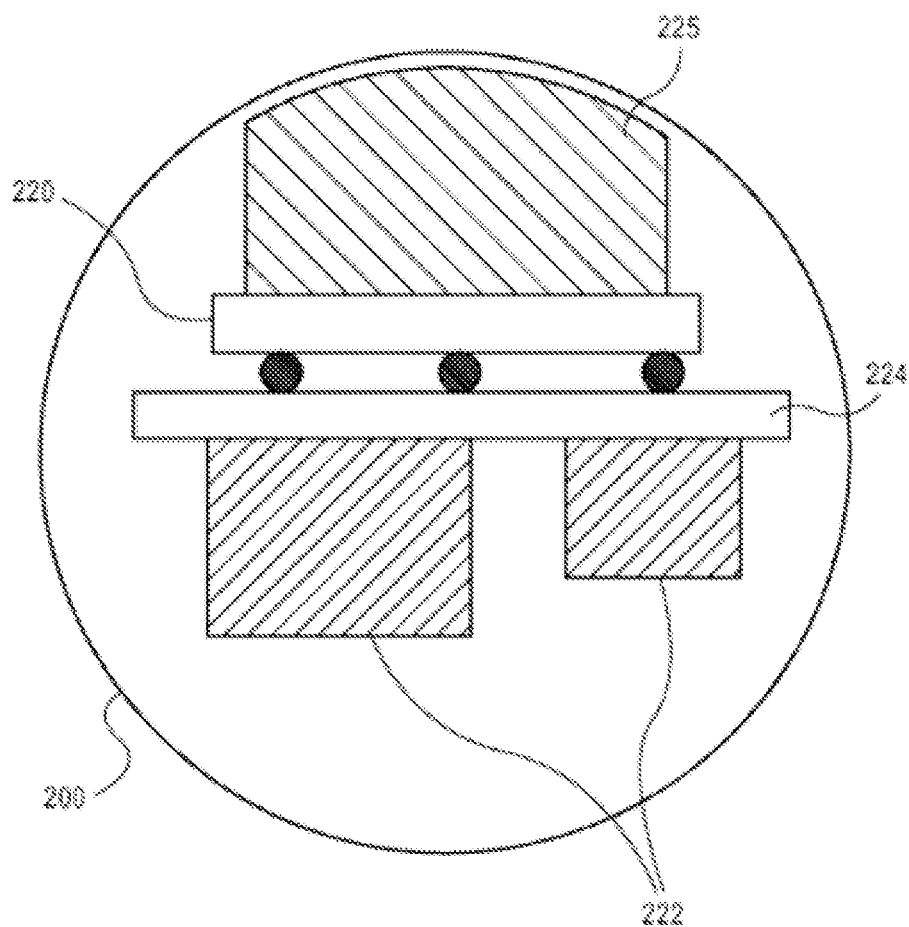

In the embodiment of FIG. 2B, the temperature sensor (e.g., 154 in FIG. 1B) can be a semiconductor temperature sensor integrated into ASIC 224. A thermally conductive pad 225 can extend from the temperature sensor in ASIC 224 to an interior surface of housing 200. Thus, the temperature sensor can sense the temperature of blood surrounding the biostimulator through housing 200 with conductive pad 225. As in the embodiment of FIG. 2A, at least two electrodes can be supported by, and exterior to, the housing. The ASIC controller 220 can be adapted to sense intracardiac information using the electrodes and to deliver stimulation energy from the battery to one of the electrodes using temperature information from the integrated temperature sensor.

Figure 2C:
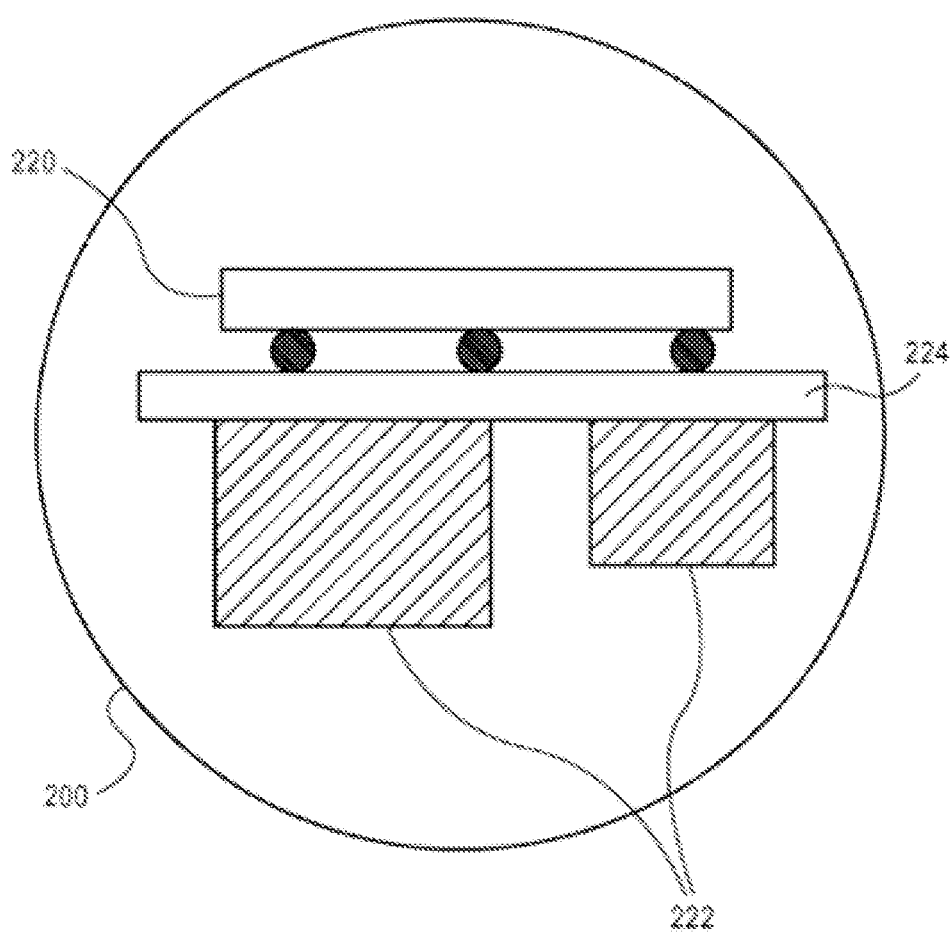

The embodiment of FIG. 2C is similar to that of FIG. 2B, but omits the thermally conductive pad. Thus, the temperature sensor (e.g., 154 in FIG. 1B) integrated into ASIC 224 senses the temperature of blood surrounding the biostimulator via the thermal conductance between the ASIC 224 and the can 202. Similarly, in this embodiment, the ASIC controller 220 can be adapted to sense intracardiac information using the electrodes and to deliver stimulation energy from the battery to one of the electrodes using temperature information from the integrated temperature sensor.

Figure 3:
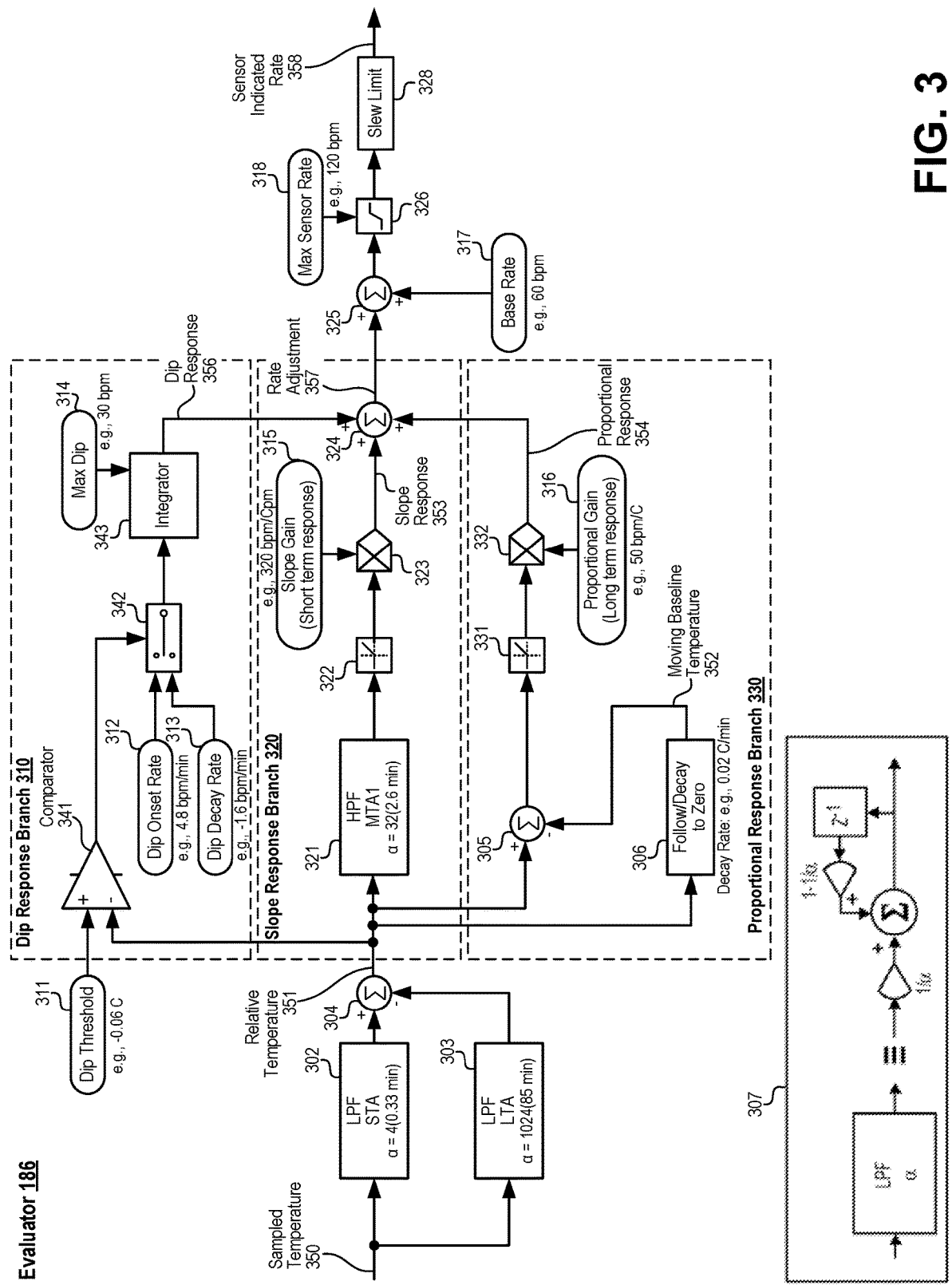
FIG. 3 is a block diagram of an embodiment of a temperature responsive controller.

Turning to FIG. 3, a block diagram illustrates a configuration of an evaluator 186 (introduced in FIG. 1B), used to provide a sensor indicated rate for pacing a heart according to certain embodiments of the disclosure. In the below description of FIG. 3, it is assumed that the components shown therein, e.g., filters, summers, integrators, etc., are implemented in the digital domain using digital circuitry, software, and/or firmware. However, it is noted that in alternative embodiments of the present technology the evaluator 186 can instead be implemented using analog components. With that said, unless stated otherwise, it will be assumed that the components shown in and described with reference to FIG. 3 are implemented in the digital domain. In the embodiments described herein it is assumed that the blood temperature measured by a temperature sensor is the same or substantially the same as the core body temperature. Accordingly, the terms blood temperature and core body temperate may be used interchangeably.

Relative Temperature

Referring to FIG. 3, a blood temperature signal 350 is provided from a temperature sensor to the inputs of low-pass filters 302 and 303 of the evaluator 186. The logic 120 (introduced in FIG. 1B) controls the interval in which the blood temperature signal detected by temperature sensor is sampled by the evaluator 186. In this illustrative embodiment, the blood temperature signal is sampled at a sampling interval of five seconds. However, sampling intervals that are greater than or less than five seconds are also possible and within the scope of the embodiments described herein.

A low pass filter (LPF) 302 provides a short term average (STA) of the blood temperature signal 350 to a non-inverting (+) input of an adder 304, which can also be referred to as a summer 304. The non-inverting (+) input of the adder 304 can also be referred to as the positive input of the adder 304. In this example, the LPF 302 has a time constant of 0.33 minutes. The LPF 302 is intended to remove noise from the blood temperature signal, where changes in blood temperature with a shorter interval than 0.33 minutes are attributed to noise, not exercise or other activity. The LPF 302 also increases the effective resolution of the temperature measurement. The LPF 302 may be a first-order low-pass filter, but is not limited thereto. The use of shorter or longer time constants for the LPF 302 are possible and within the scope of the embodiments described herein.

A LPF 303 provides a long term average (LTA) of the blood temperature signal 350 to an inverting (−) input of adder 304. The inverting (−) input of the adder 304 can also be referred to as the negative input of the adder 304. The LPF 303 has a time constant of 85 minutes in certain embodiments. The output of LPF 303 is intended to follow the baseline blood temperature in the absence of exercise or other activity, where changes in blood temperature with a longer interval than 85 minutes are attributed to such factors as fever, diurnal variation, and measurement drift, not exercise or other activity. Accordingly, the LTA of the blood temperature signal (which is output from the LPF 303) can also be referred to as the baseline blood temperature. It is understood that other non-exercise factors may represent the source of longer term time constant changes. The use of shorter or longer time constants for the LPF 303 are possible and within the scope of the embodiments described herein.

The adder 304 outputs a relative temperature signal 351, which represents current blood temperature relative to the baseline value before exercise or other activity. More specifically, that adder 304 is used to produce the relative temperature signal 351 by subtracting the LTA (produced by the LPF 303) from the STA (produced by the LPF 302). This relative temperature signal 351 is intended to exclude noise and non-exercise factors such as fever, diurnal variation, and measurement drift. Where a person is at rest and their short term average (STA) temperature is the same as their long term average (LTA) temperature, their relative temperature 351 will be zero. When the person starts to exercise and their core body temperature initially dips, the relative temperature 351 will initially go negative, i.e., below zero. After exercising for a prolonged period of time the person's core body temperature will eventually rise such that their STA is greater than their LTA, at which point the relative temperature will go positive, i.e., above zero.

Inset 307 of FIG. 3 provides details for one exemplary embodiment of a low pass filter (LPF) of the evaluator 186. In the example of inset 307, the LPF is implemented as a linear first-order recursive digital filter. The time-constant for the filter, analogous to the time constant for a resistor-capacitor (RC) electrical filter, is approximately a (alpha) times the sampling interval (5 seconds). Inset 307 can implement any of the LPFs of the evaluator 186 in this example embodiment. The LPF shown in the inset 307 is a relatively simple single pole filter. In alternative embodiments, more a complex multi-pole LPF can be used instead, as would be understood by one of ordinary skill in the art.

In summary, the relative temperature signal 351 provides a signal representing blood temperature changes due to exercise or other activity, which is then conveyed to the inputs of three parts of the evaluator 186: the dip response, the slope response, and the proportional response. Explained another way, the relative temperature signal 351 is provided to a dip response branch 310, a slope response branch 320, and a proportional response branch 330. As can be appreciated from FIG. 3, and described in additional detail below, in accordance with certain embodiments outputs of (also referred to a signal output by) each of these branches 310, 320, and 330 are combined (e.g., summed by a summer 324) to produce a rate adjustment output 357 (also referred to as a rate adjustment signal 357), which is used to produce a sensor indicate rate response signal 358. Additional details of each of the branches 310, 320, and 330 of the evaluator 186 will now be described.

Dip Response

When a person changes from an inactive or resting state to an active state, the person's core body temperature will typically drop from a baseline or first core body temperature to a second core body temperature. In other words, initially there is typically a small dip in the person's core body temperature. This small dip in the person's core body temperature is caused by vasodilation at an onset or anticipation of exercise or other activity. Explained another way, the small dip at the onset of exercise is due to cooler blood flowing to the heart from the periphery of the body where blood is cooler. This initial drop (also referred to as dip) in the core body temperature is typically followed by a rise in the core body temperature, or by a brief leveling off period followed by a rise in the core body temperature. If the activity is brief the core body temperature will typically slowly return to its baseline core body temperature. However, if the activity (e.g., exercise) continues, the core body temperature will rise past the baseline core body temperature to an elevated core body temperature that will typically continue to rise until a maximum is reached or the activity ceases. After the activity ceases, the core body temperature will typically slowly return to the baseline core body temperature.

Embodiments of the present technology utilize a dip response to take into account the characteristic that a person's core body temperature will typically experience a dip at the onset of activity (e.g., exercise). The dip response branch 310 shown in FIG. 3 illustrates an implementation of the dip response, according to certain embodiments of the present technology.

Referring to FIG. 3, the dip response is implemented in this illustrative embodiment by a comparator 341 and an integrator 343 included in the dip response branch 310 of the evaluator 186. The comparator 341 is shows as including an inverting (−) input and a non-inverting (+) input (which can also be referred to respectively as negative and positive inputs) and an output. The inverting (−) input of the comparator 314 is provided with the relative temperature signal 351 and the non-inverting (+) input of the comparator 314 is provided with a dip threshold 311, e.g., stored in a register or some other storage element. An exemplary value for the dip threshold is −0.06 degrees Celsius (° C.), but higher or lower values for the dip threshold can alternatively be used. A switch 342, which is controlled by the output of the comparator 341, provides either a dip onset rate value 312 (e.g., 4.8 bpm/min) to an input of the integrator 343, or a dip decay rate value 313 (e.g., −1.6 bpm/min) to the input of the integrator 343. Each of the dip onset rate value 312 and the dip decay rate value 313 can be stored in a respective register or some other storage element. Other values for the dip onset rate value 312 and the dip decay rate value 313, besides the exemplary values specified above, can alternatively be used. Each of the dip threshold 311, the dip onset rate 312, and the dip decay rate 313 can be programmable and stored in a respective register or memory location such that they are customizable for a specific person.

When the magnitude of the relative temperature signal 351 is greater than the dip threshold (e.g., −0.06° C.), then the output of the comparator will be LOW, and the switch 342 will be controlled to provide the dip decay rate (e.g., −1.6 bpm/min) to the integrator 343. When the magnitude of the relative temperature signal 351 transitions to being less than the dip threshold (e.g., −0.06° C.), which is indicative of the onset of exercise, the output of the comparator will go HIGH, and the switch 342 will be controlled to provide the dip onset rate 312 (e.g., 4.8 bpm/min) to the input of the integrator 343.

The integrator 343 is configured to integrate the signal received at its input, which signal is either the dip onset rate 312 or the dip decay rate 313, as selected by the switch 342 that is controlled by the output of the comparator 341. In accordance with certain embodiments, the integrator 343 is configured to generate an output only when the result of its integrating is positive. Alternatively the integrator 343 can generate both positive and negative outputs, and a rectifier (e.g., similar to the rectifier 322 discussed below) can receive the output of the integrator 343 to provide only the positive component of the output of the integrator 343 to the summer 324. Either way, the dip response signal 356 that is generated by the dip response branch 356 should either be a positive signal or zero. Since the integrator 343 is part of the dip response branch 310, it can also be referred to more specifically as the dip integrator 343.

As shown in FIG. 3, the dip response signal 356 that is generated by the dip response branch 310 is provided to a summer 324, which sums the dip response signal 356 with a slope response signal 353 and a proportional response signal 354 (produced respectively by the branches 320 and 330) to produce a rate adjustment signal 357. The rate adjustment signal 357 is added to a base rate 317 to produce a sensor indicated rate 358, as will be described in additional detail below. In accordance with certain embodiments, the integrator 343 is configured such that its output cannot exceed a maximum dip response, e.g., 30 bpm, in order to limit how much the sensor indicated rate 358 can be increased in response to the onset of exercise. The maximum dip 314 can be stored in a register or some other storage element and can be programmable such that it can be customized for a specific person.

As explained above, when the relative temperature 351 falls below the dip threshold 311, the dip integrator 343 ramps up at the dip onset rate. The integrator 343 will stop at a level set by the max dip 314. In accordance with certain embodiments, when the dip subsides, such that the relative temperature 351 is above the dip threshold 311, the comparator 341 and the switch 342 will cause the dip decay rate 313 (rather than the dip onset rate 312) to be provided to the input of the dip integrator 343, and the dip integrator 343 will linearly decay the output of the integrator at the dip decay rate 313 (e.g., −1.6 bpm/min), until eventually the dip response 356 will return to zero. In alternative embodiments, the output of the integrator 343 may be increased and/or decreased non-linearly.

The dip integrator 343 preferably provides for an increase in the dip response 356, in response to the onset of exercise, that is gradual. Additionally, the dip integrator 343 preferably maintains the dip response 356 above zero for a while beyond the onset of exercise, and provides for heart rate increases during a prolonged dip.

In accordance with certain embodiments, a high pass filter (HPF) can be included in the dip response branch 310 in order to filter the relative temperature signal 351 prior to providing it to the inverting (−) input of the comparator. Such an added HPF can have an exemplary time constant of 10 minutes, but is no limited thereto. The purpose of the added HPF would be to limit the time extent of the dip response.

Slope Response

The slope response 353 provided by the slope response branch 320 is intended to provide a short-term response during an upswing of the relative temperature 351 several minutes into exercise, following the initial dip in the relative temperature. Still referring to FIG. 3, in the embodiment shown therein the slope response branch 320 is shown as including a high pass filter (HPF) 321, a rectifier 322, and a multiplier 323. A bandpass filter (BPF) can be used in place of the HPF 321, in which case it is also possible that a combination of a LPF and a HPF can be used to implement such a BPF.

When the relative temperature 351 is increasing, this indicates that exercise is warming the blood, and the rate of increase of temperature (i.e. the slope) is an indication of the level of exercise. The HPF 321 essentially acts as a slope detector, such that its output is indicative of the slope of the relative temperature signal 351. The rectifier 322, which is downstream of the HPF 321, passes only positive slope values to the multiplier 323, and provides a zero to the multiplier 323 when a slope value is negative. The multiplier 322 multiplies positive slope values output by the HPF 321 by a slope gain 315 to provide the slope response 353. An exemplary value for the slope gain 315 is 320 bpm per degree C. per minute (bpm/° C./min), but higher and lower values can be used. The slope gain 315 can be stored in a register or some other storage element, and can be programmable such that is can be customized for a specific person. In alternative embodiments, instead of multiplying positive slope values by a slope gain (315) to produce the slope gain response, a predetermined function can be applied to the positive slope values to produce the slope response signal 353. An example of such a function is a piece-wise-linear function having two parts, including a first part having an initial slope of 320 bpm/° C./min, and a second part (e.g., for relative temperature values greater than 0.1° C.) having a slope of 160 bpm/° C./min. Other variations are also possible and within the scope of the embodiments described herein.

In accordance with alternative embodiments, an alternative type of slope detector can be used in place of the HPF 321. For example, an alternative slope detector can determine a difference between two values of the relative temperature 351, and divide the difference in values by a difference in sample times corresponding to the two values. Other techniques for detecting slope are also possible, as would be known to one of ordinary skill in the art, and are with the scope of the embodiments disclosed herein.

So long as the relative temperature 351 is increasing, the slope response 353 should have a positive value and will contribute to the rate adjustment 357. However, when relative temperature 351 is not increasing, the slope response 353 should be zero, and will not contribute to the rate adjustment 357.

Proportional Response

The proportional response, which is produced by the proportional response branch 330, is computed using the relative temperature 351 minus a moving baseline 352. Referring to FIG. 3, the long term average temperature, which is output by the LPF 303, can also be referred to as a baseline temperature since it is indicative of the baseline core body temperature over a relative long period of time, e.g., 85 minutes. By contrast, within the proportional response branch 330 the moving baseline temperature 352 that is generated follows the downward dip of the relative temperature 351. When the dip ends, the moving baseline is allowed to gradually return back to zero, in a linear or non-linear fashion. This quantity represents the body core temperature baseline, taking into account the drop in the core body temperature due only to the peripheral drop. In other words, it is the core temperature if there was no exercise or other activity.

Still referring to FIG. 3, the proportional response branch 330 is shown as including a summer 305, a follow/decay to zero block 306, a rectifier 331, and a multiplier 332. The relative temperature 351 is provided to a positive input of the summer 305, as well as to the bock 306. In accordance with an embodiment, the output of the block 306, which is the moving baseline temperature 352, follows the relative temperature 351 during a drop in the relative temperature 351, and is provided to a negative input of the summer 305. So long as the relative temperature is dropping and negative, the output of the summer 305 will be zero. For example, if the relative temperature is −0.01, then the output of block 206 will also be −0.01, in which case the summer 305 will perform the calculation sum=−0.01−(−0.01)=−0.01+0.01=0. Once the relative temperature starts increasing (after reaching is minimum, i.e., maximum dip) then the moving baseline temperature 352 will lag the relative temperature signal, and the output of the summer 305 will remain positive for at least a portion of the time during which the patient remains active, as the moving baseline temperature 352 decays toward zero.

The summer 305 subtracts the moving baseline temperature signal 352 from the relative temperature signal 351 to produce a difference signal indicative of a difference between the relative temperature signal and the moving baseline temperature signal. The rectifier 331, which is downstream of the summer 305, passes only positive slope values of the difference signal to the multiplier 332, and provides a zero to the multiplier 332 when the difference signal is negative. The multiplier 332 multiplies positive difference values output by the summer 305 by a proportional gain 316 to provide the proportional response 354. An exemplary value for the proportional gain 316 is 50 bpm/° C./min, but higher and lower values can be used. The proportional gain 316 can be stored in a register or some other storage element, and can be programmable such that is can be customized for a specific person. In alternative embodiments, instead of multiplying positive difference values by a proportional gain (316) to produce the proportional response, a predetermined function can be applied to the positive difference values to produce the proportional response signal 354. An example of such a function is a piece-wise-linear function having two parts, including a first part having an initial slope of 50 bpm/° C./min, and a second part (e.g., for relative temperature values greater than 0.2° C.) having a slope of 25 bpm/° C./min. Other variations are also possible and within the scope of the embodiments described herein.

Rate Adjustment and Sensor Indicated Rate

As shown in FIG. 3, the dip response 356, the slope response 353, and the proportional response 354 are summed by the summer 324 to produce a rate adjustment signal 357. The summer 324 adds a base rate (e.g., 60 bpm) to the rate adjustment signal to produce a sensor indicated rate 358. A limiter 326 limits the sensor indicated rate 358 to a maximum sensor rate (e.g., 120 bpm). A slew limiter 328 limits the rate of change of the sensor indicated rate 358. The slew limiter 328 can be implemented, e.g., using a low pass filter (LPF) with a short-term averaging time constant of 0.33 minutes, to prevent abrupt changes in pacing rate. The sensor indicated rate 358 is output to logic 120 (in FIG. 1B), which adjusts and/or delivers therapy by sending a control signal to a pulse generator 116 for generating pacing pulses for delivery via the electrodes 104 and 106. In certain embodiments, the pacemaker may use the sensor indicated rate to adjust the pacing rate.

Although the logic 120 and the evaluator 186 are illustrated as separate modules of FIG. 1B, the logic 120 and the evaluator 186 may be incorporated into a single processing unit. The evaluator 186 and any of its components discussed in greater detail herein may be components of or modules executed by the logic 120.

The slope gain 315, the proportional gain 316, the maximum dip 314, and/or the maximum sensor rate 318 can be preprogrammed with default values that are based on a patient's age and/or health. Such values can be customized for a particular patient based on the "Wilkoff model" or some other appropriate physiological exercise model of chronotropic response that provides appropriate predictive heart rates for given levels of exertion in the particular patient. Heart rates appropriate for a plurality of exertion levels may be derived from the model, either by the biostimulator 100, or by a programmer that communicates with and programs the biostimulator 100, and may be stored in the biostimulator or programmer as a table, or the like. The biostimulator 100 may then be programmed to record over time a heart rate profile along with an exertion level profile determined from an exertion level sensor such as an accelerometer or minute ventilation sensor. By comparing the recorded heart rate profile with predictive heart rates from the model, the biostimulator can determine if and when a change in chronotropic status occurs.

Exemplary Graphs

The dip response 356 signal, the slope response signal 353, and the proportional response signal 354 can be referred to respectively, more succinctly, as the dip response 356, the slope response 353, and the proportional response 354. Similarly, the rate adjustment signal 357 can be referred to more succinctly as the rate adjustment 357, and the sensor indicated rate signal 358 can be referred to more succinctly as the sensor indicated rate 358.

Figure 4B:
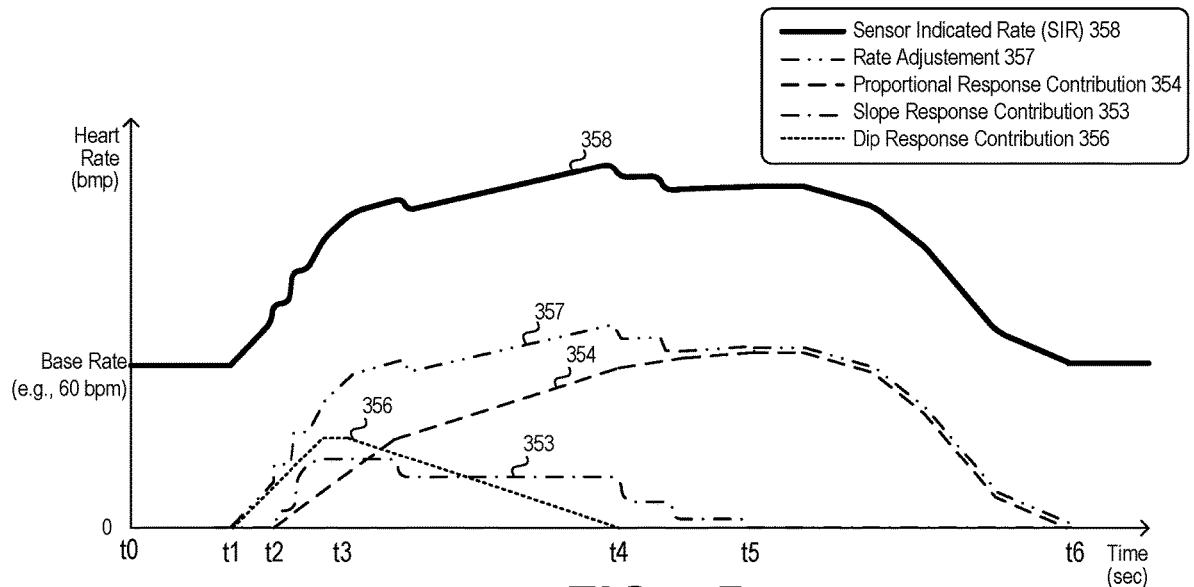
FIG. 4B is a graph that shows an exemplary dip response, an exemplary slope response, and an exemplary proportional response can be combined with one another and a base rate to produced sensor indicated rate (SIR) response.
Figure 4A:
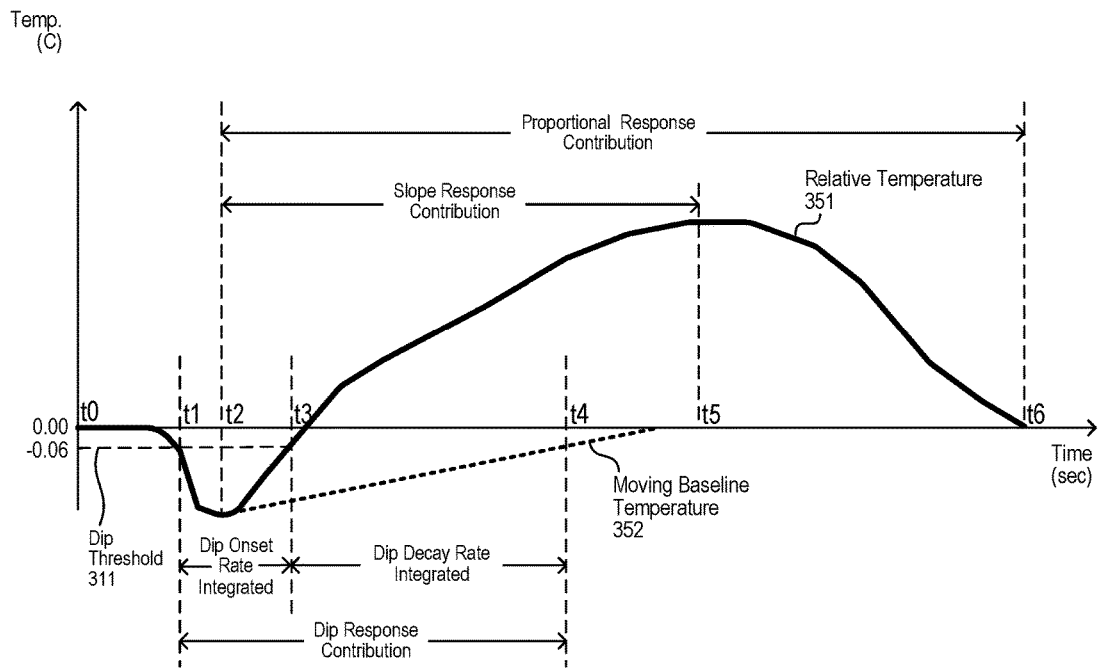
FIG. 4A is a graph that shows how a relative temperature sensed using an implanted temperature sensor may change over time.

FIGS. 4A and 4B are exemplary graphs that are used to show how the dip response 356, the slope response 353, and the proportional response 354 (each of which were initially discussed above with reference to FIG. 3) may collectively contribute to producing the rate adjustment 357 and the sensor indicated rate 358 for an exemplary person.

FIG. 4A shows how the relative temperature 351, sensed using an implanted temperature sensor, may change over time. More specifically, FIG. 4A shows that there is initially a small dip in the relative temperature 351 at the onset of exercise or other activity, followed by a rise in the relative temperature 351, followed by a brief leveling off period, followed by a slow or gradual return to zero. FIG. 4A also illustrates how during different periods of time the dip response 356, the slope response 353, and the proportional response 354 may contribute to producing the rate adjustment 357 and the sensor indicated rate 358. FIG. 4B shows an exemplary dip response 356, an exemplary slope response 353, and an exemplary proportional response 354, as well as how an exemplary rate adjustment 357 can be produced by adding the aforementioned responses (at the summing node 324 in FIG. 3), and how an exemplary sensor indicated rate (SIR) 358 can be produced by adding the rate adjustment 357 to a base rate 317 (at the summing node 325 in FIG. 3). In FIGS. 4A and 4B, it is assumed that the max sensor rate 318 is not exceeded. Also, it is noted that the waveforms in FIGS. 4A and 4B are not drawn to scale, but rather, are used as an illustrative example of how embodiments of the present technology may combine three responses with the base rate 325 to produce the sensor indicated rate (SIR) 358.

Referring to FIG. 4A, the relative temperature 351 is shown as starting at 0.00° C. at time t0, and then dropping to the dip threshold 311 at time t1. The relative temperature 351 is shown as continuing to drop until time t2, at which point it begins to rise until it increases to the dip threshold at time t3. Due to continued exercise or other activity, the relative temperature 351 continues to rise until it plateaus at time t5, which may correspond to a point at which the person stops exercising or otherwise rests. Between times t5 and t6 the relative temperature 351 is shown as dropping until it reaches 0.00° C. at time t6. Also shown in FIG. 4A is an example of the moving baseline temperature 352 output by the block 306 in FIG. 3.

Referring to FIG. 4B, the dip response 356 is shown as rising from 0 bpm at time t1 to its maximum between times t2 and t3, in response to the dip onset rate 312 being integrated (by the integrator 343) when the relative temperature is below the dip threshold 311. The dip response 356 is then shown as dropping from its maximum back 0 bpm at time t4, in response to the dip decay rate 313 being integrated (by the integrator 343) when the relative temperature exceeds the dip threshold 311.

In FIG. 4B, the slope response 353 is shown as rising from the point at which the relative temperature has a positive slope, at time t2, until the relative temperature plateaus at time t5.

In FIG. 4B, the proportional response 354 is shown as rising from 0 at the time t2 until the time t5, and then decaying at a decay rate (e.g., 0.02° C./min) back to 0 at time t6.

In FIG. 4B, the rate adjustment 357 (produced by the summer 324 in FIG. 3) is produced by summing the dip response 356, the slope response 353, and the proportional response 354. The sensor indicated rate 358 is produced by adding the rate adjustment 357 to the base rate, e.g., 60 bpm. As noted above, it is assumed that the max sensor rate 318 is not exceeded. Although not specifically shown in FIG. 4B, the upward and downward slope of the sensor indicated rate 358 may be reduced (i.e., made shallower) by the slew limiter 328.

Methods

Figure 5:
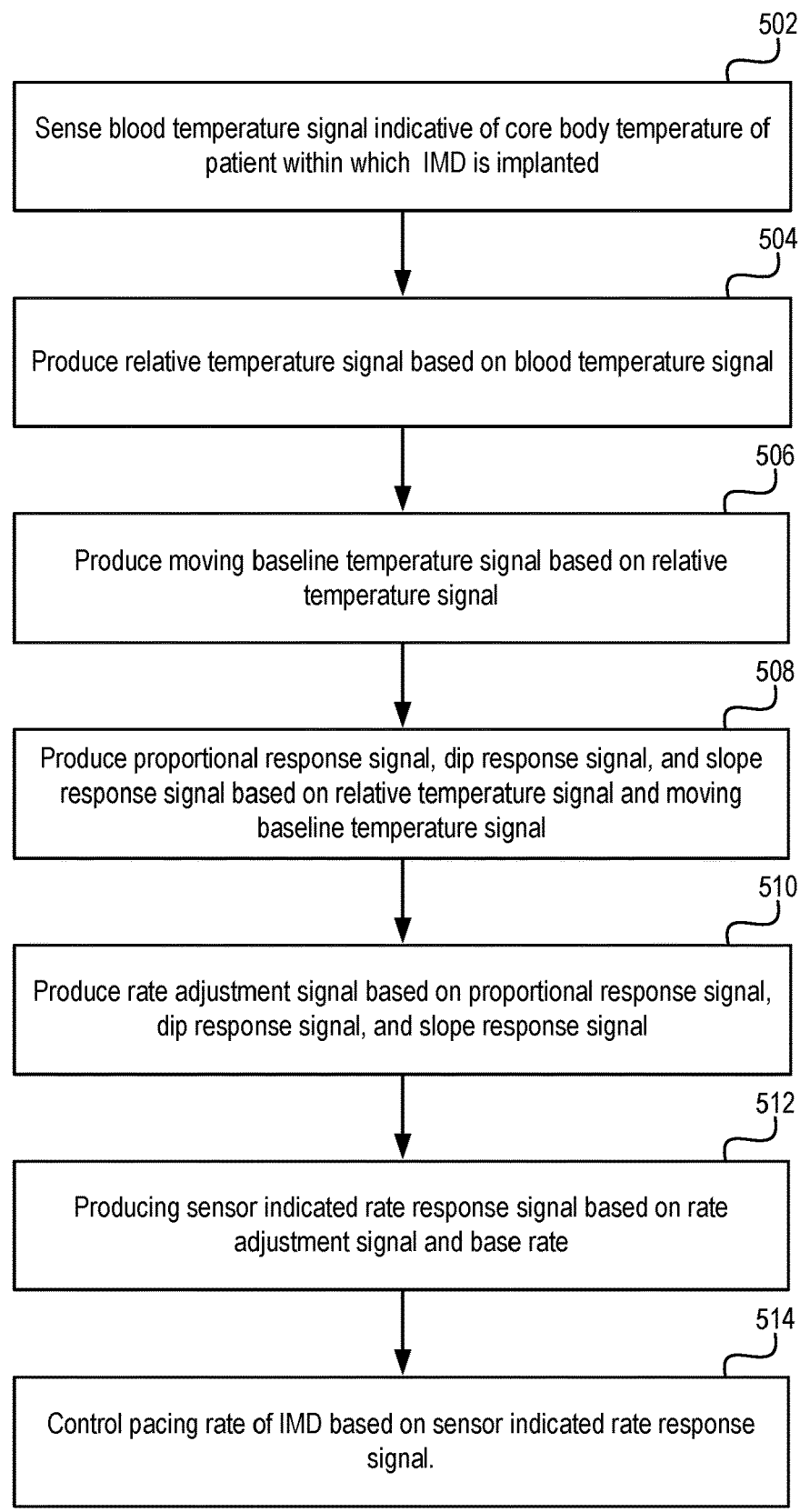
FIG. 5 is a high level flow diagram that is used to summarize methods according to various embodiments of the present technology that can be used to provide a temperature based rate response for a patient within which an implantable medical device (IMD), such as the leadless pacemaker introduced in FIGS. 1A and 1B, is implanted.

FIG. 5 is a high level flow diagram that is used to summarize methods according to various embodiments of the present technology that can be used to provide a temperature based rate response for a patient within which an implantable medical device (IMD), such as the biostimulator 100, or more generally an implantable medical system, is implanted. Methods described in conjunction with flow diagrams (also known as flow charts) presented herein may be implemented, e.g., in a non-transitory computer-readable medium that includes instructions for causing a programmable processor to carry out the methods described. The instructions may be implemented as one or more software modules, which may be executed by themselves or in combination with other software.

Referring to FIG. 5, step 502 involves sensing a blood temperature signal indicative of a core body temperature of the patient within which the IMD is implanted. Referring briefly back to FIG. 3, the blood temperature signal 350 shown therein is an example of the blood temperature signal that can be sensed at step 502. The blood temperature signal can, e.g., be sampled at a sampling interval of five seconds. However, sampling intervals that are greater than or less than five seconds are also possible and within the scope of the embodiments described herein. Exemplary temperature sensors that can be used to sense a blood temperature signal were described above.

Referring again to FIG. 5, step 504 involves producing a relative temperature signal based on the blood temperature signal. Referring briefly back to FIG. 3, the relative temperature signal 351 shown therein is an example of the relative temperature signal that can be produced at step 504. In accordance with certain embodiments, the relative temperature signal can be produced by producing a short term average (STA) of the blood temperature signal, producing a long term average (LTA) of the blood temperature signal, and producing the relative temperature signal by subtracting the LTA of the blood temperature signal from the STA of the blood temperature signal. As shown in FIG. 3, The STA of the blood temperature signal can be produced using the LPF 302, the LTA of the blood temperature signal can be produced using the LPF 303, and the summer 304 can be used to subtract the LTA of the blood temperature signal from the STA of the blood temperature signal to thereby produce the relative temperature signal 351.

Referring again to FIG. 5, step 506 involves producing a moving baseline temperature signal based on the relative temperature signal. Referring briefly back to FIG. 3, the moving baseline temperature signal 352 is an example of the results of step 506, and the block 306 can be used to produce the moving baseline temperature signal 352. In accordance with certain embodiments, the moving baseline temperature signal follows the relative temperature signal during the initial drop in the blood temperature signal that occurs during an onset of activity, and the moving baseline temperature signal decays towards zero during an upswing in the blood temperature signal that follows the initial drop in the blood temperature signal.

Referring to FIG. 5, step 508 involves producing a proportional response signal, a dip response signal, and a slope response signal based on the relative temperature signal. Referring briefly back to FIGS. 3 and 4, the proportional response signal 354, the dip response signal 356, and the slope response signal 353 shown therein are examples of the signals produced at step 508. Additional details of how to produce such signal are described above with reference to FIGS. 3 and 4, and are also discussed below.

Referring to FIG. 5, step 510 involves producing a rate adjustment signal based on the proportional response signal, the dip response signal, and the slope response signal. Referring briefly back to FIGS. 3 and 4, the rate adjustment signal 357 shown therein can be produced by summing the proportional response signal 354, the dip response signal 356, and the slope response signal 353. Alternative ways of combining the signals are also possible and within the scope of the embodiments described herein.

Referring to FIG. 5, step 512 involves producing a sensor indicated rate response signal based on the rate adjustment signal and a base rate. Referring briefly back to FIGS. 3 and 4, the sensor indicated rate response signal 358 shown therein can be produced by summing the rate adjustment signal 357 and the base rate 317. Alternatively, the sensor indicated rate can be produced by summing the proportional response signal 354, the dip response signal 356, the slope response signal 353, and the base rate. In other words, the step of producing the rate adjustment signal can be skipped, and rather, the proportional response signal 354, the dip response signal 356, the slope response signal 353, and the base rate 317 can be combined (e.g., added) in a single step. It is also within the scope of the embodiments described herein to combine the proportional response signal with only one of the dip response signal 356 and the slope response signal 353. For example, only the larger of the dip response signal 356 and the slope response signal 353 can be used, or just a predetermined one of the two can be used. In accordance with certain embodiments, a magnitude and/or a slew rate of the sensor indicated rate response signal is/are limited, e.g., using the limiters 326 and/or 328 in FIG. 3. Finally, step 514 in FIG. 5 involves controlling a pacing rate of the IMD based on the sensor indicated rate response signal. This can involve, e.g., increasing or decreasing a rate at which pacing pulses are generated and delivered via one or more electrodes to cause pacing of a patient's heart.

In accordance with certain embodiments, the proportional response signal, produced at step 508, is produced by subtracting the moving baseline temperature signal from the relative temperature signal to produce a difference signal indicative of a difference between the relative temperature signal and the moving baseline temperature signal, and producing the proportional response signal based on positive portions of the difference signal. In certain embodiments, the proportional response signal is produced based on positive portions of the difference signal by multiplying positive portions of the difference signal by a proportional gain value (e.g., 316 in FIG. 3) to thereby produce the proportional response signal. Alternatively, a predetermined function can be applied to positive portions of the difference signal to thereby produce the proportional response signal. An example of such a function was discussed above.

In accordance with certain embodiments, the proportional response signal provides for an increase in the pacing rate, based on a difference between the relative temperature signal and the moving baseline temperature signal, during an upswing in the blood temperature signal that follows an initial drop in the blood temperature signal that occurs during the onset of activity. Additionally, the proportional response provides for a decrease in the pacing rate, based on the difference between the relative temperature signal and the moving baseline temperature signal, during a downswing in the blood temperature signal that occurs in response to a reduction or cessation in activity.

In accordance with certain embodiments, the dip response signal provides for an increase in the pacing rate during the initial drop in the blood temperature signal that occurs during an onset of activity. In accordance with certain embodiments, the dip response signal is produced by comparing the relative temperature signal (e.g., 351 in FIG. 3) to a dip threshold (e.g., 311 in FIG. 3). A dip onset rate value (e.g., 312 in FIG. 3) is provided to an input of an integrator (e.g., 343 in FIG. 3) while the relative temperature signal is less than the dip threshold, and a dip decay rate value (e.g., 313 in FIG. 3) is provided to the input of the integrator while the relative temperature signal is greater than the dip threshold. Positive portions of a signal output by the integrator can then be used as the dip response signal. In certain embodiments, the integrator (e.g., 343 in FIG. 3) can be designed to output a zero when the result of its integration is negative. Alternatively, the output of the integrator can be provided to a rectifier so that only positive outputs of the integrator contribute to the dip response signal. The former embodiment is preferable, as it avoids "wind-up" where the integrator internal value goes past the limit and retains that excess value. The integrator could alternatively be implemented by using a low pass filter instead of a pure integrator. It would then behave as a "leaky" integrator, which could have some advantages.

In accordance with certain embodiments, the slope response signal provides for an increase in the pacing rate, based on a slope of the relative temperature signal, during an upswing in the blood temperature signal that follows an initial drop in the blood temperature signal. In accordance with certain embodiments, the slope response signal can be produced by producing a signal indicative of a positive slope of the relative temperature signal, and multiplying the signal indicative of the positive slope of the relative temperature signal by a slope gain value (e.g., 315 in FIG. 3) to thereby produce the slope response signal (e.g., 353 in FIG. 3). Alternatively, a predetermined function can be applied to the signal indicative of the positive slope of the relative temperature signal to thereby produce the slope response signal. An example of such a function was discussed above. In accordance with certain embodiments, the signal indicative of the positive slope of the relative temperature signal is produced by providing the relative temperature signal to a HPF (e.g., 321 in FIG. 3) to thereby produce a signal indicative of a slope of the relative temperature signal, and providing an output of the HPF to a rectifier (e.g., 322 in FIG. 3) to thereby produce the signal indicative of the positive slope of the relative temperature signal. Alternatively, the signal indicative of the positive slope of the relative temperature signal is produced by determining a difference between two temporally different samples of the relative temperature signal, and producing the signal indicative of the positive slope of the relative temperature signal based on the difference. Other variations are also possible and within the scope of the embodiments described herein.

Figure 6:
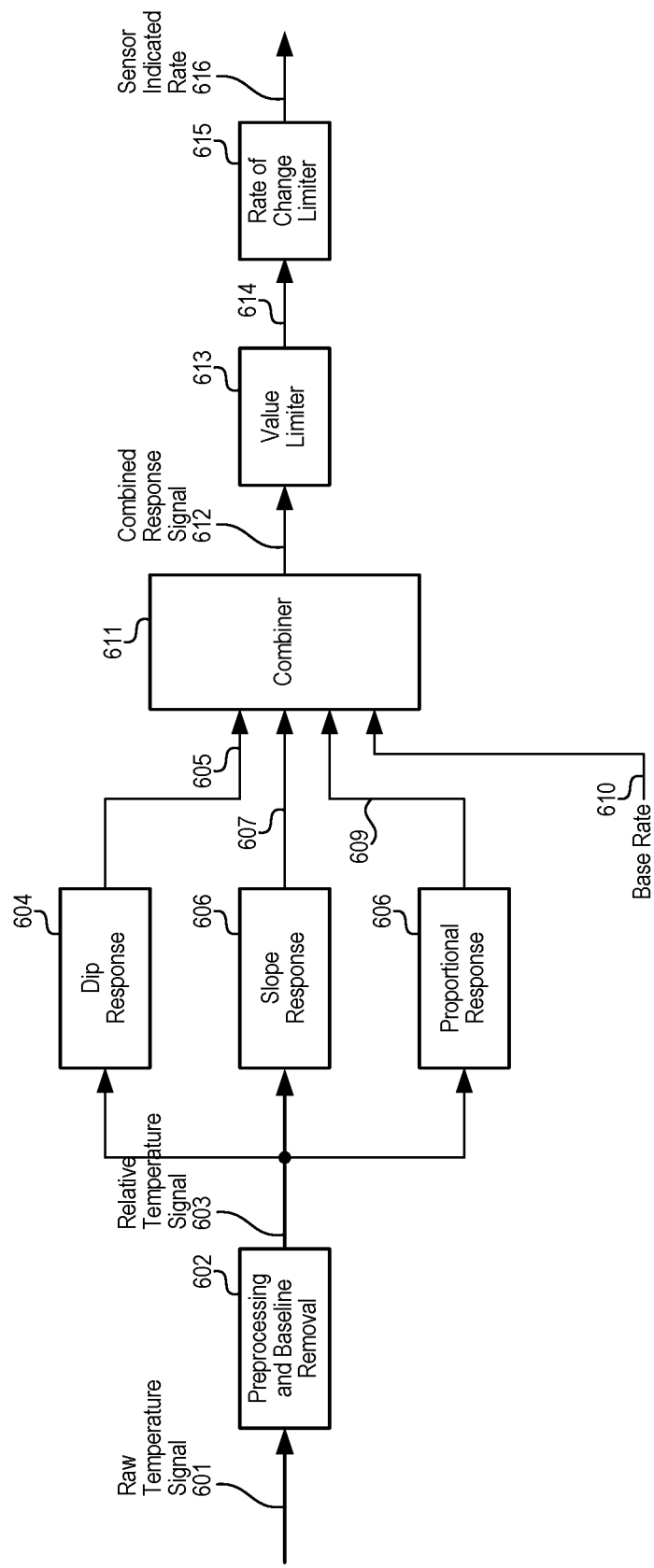
FIG. 6 illustrates a block diagram implementing a Rate Response process in accordance with various embodiments herein.

FIG. 6 illustrates a block diagram implementing a Rate Response process in accordance with embodiments herein. By way of example, the blocks illustrated in FIG. 6 may be implemented in one of, or with a combination of, hardware, circuitry, and/or microprocessors implementing firmware and/or software instructions. As a further example, the blocks illustrated in FIG. 6 may be implemented through circuitry, such as the general circuitry illustrated in FIG. 3, as may be referenced hereafter as examples. However, it is understood that the block diagram of FIG. 6 is not limited to the circuitry implementation of FIG. 3.

A blood temperature measurement signal 601 is provided by the temperature sensor and serves as input to a Preprocessing and Baseline Removal (PBR) block 602. The PBR block 602 is configured to perform noise reduction (e.g. filtering) from the raw measurement signal 601 and to generate a Relative Temperature signal 603 that is determined or derived relative to a baseline. The Relative Temperature signal 603 is fed into three processing blocks, Dip Response 604, Slope Response 606, and Proportional Response 608. The Dip Response 604, Slope Response 606, and Proportional Response 608 may be implemented in parallel (as shown), in series or a combination thereof. When implemented in series, the Dip 604, Slope Response 606, and Proportional Response 608 may be implemented in various orders.

The Dip Response 604 is configured to manage a rapid initial increase in heart rate based on the initial drop in the blood temperature, when the patient is in an exercise onset state (e.g., beginning to perform exercise). When an initial drop (i.e., dip) in blood temperature is detected that is indicative of an exercise onset state, the Dip Response 604 generates a Dip Response signal 605 indicating that the heart rate should be increased.

The Slope Response 606 is configured to manage a target rate of increase in the heart rate relative to a rate at which the blood temperature is increasing. When an increase in blood temperature is detected, the Slope Response 606 analyzes the rate of change in the blood temperature over a select time period. When in an initial phase of exercise state, the Slope Response 606 generates a Slope Response signal 607 indicative of a rate of change in the target heart rate that is indicative of the rate at which the blood temperature increases.

The Proportional Response 608 is configured to manage heart rate increase during a sustained exercise state. To do so, in accordance with certain embodiments the Proportional Response 608 does not contribute to the rate response during the initial dip of the core body temperature at the onset of activity, but contributes thereafter to the rate response during increases in the core body temperature in a manner that is proportional to a difference between the relative temperature and the moving baseline temperature. In accordance with certain embodiments, the Proportional Response provides for an increase in the pacing rate, based on a difference between the relative temperature signal and the moving baseline temperature signal, during an upswing in the blood temperature signal that follows an initial drop in the blood temperature signal that occurs during the onset of activity. Additionally, the Proportional Response provides for a decrease in the pacing rate, based on the difference between the relative temperature signal and the moving baseline temperature signal, during a downswing in the blood temperature signal that occurs in response to a reduction or cessation in activity.

The three signals 605, 607, and 609 are provided as inputs to the Combiner 611, which combines the signals 605, 607 and 609 in a predetermined manner to form a combined response 612 that is indicative of an overall heart rate increase and/or target heart rate based on whether the patient is in an exercise onset state, an initial phase of exercise, a sustained exercise state or a non-exercise state. The Base Rate 610 is also an input to the Combiner 611, such that when there is no need for a rate increase, the Combined Response signal 612 can be set to the Base Rate 610. An exemplary Base Rate is 60 bpm, but higher or lower Base Rates are also possible, depending upon the patient.

The Combined Response signal 612 is provided as an input to the Value Limiter block 613 which functions to limit the range of values of the target heart rate for the safety of the patient. The output of the Value Limiter 614 serves as input to the Rate-of-change Limiter 615. The function of the Rate-of-change Limiter 615 is to limit the rate of change of the target heart rate thereby prevent sudden changes in heart rate. The output of the Rate-of-change Limiter 615 is the Sensor Indicated Rate 616, which is utilized by the pacemaker to set the target pacing rate.

In certain embodiments, the processing blocks are rearranged to arrive at embodiments that work equivalently or similarly. For example, in FIG. 6, the Base Rate 610 is shown entering the Combiner 611. Since the Base Rate is a static value, it is possible to instead combine the Base Rate 610 with the output of the Rate-of-change Limiter 615 and change the range of the Value Limiter 613 to achieve an equivalent result.

Each of the blocks shown in FIG. 6 may have alternative embodiments. Each embodiment may have different characteristics, which allow making tradeoffs among performance, complexity, code size, and so on. It is recognized that the various combinations of the blocks will result in alternative embodiments for the entire algorithm. The following paragraphs describe some alternative embodiments of the different processing blocks, including the preferred embodiment.

The PBR block 602 is configured to perform preprocessing to reduce any noise in the raw temperature signal. The PBR block 602 also increases the effective resolution of the temperature measurement. With reference to FIG. 3 in a certain embodiment, the preprocessing may be performed by a LPF 302. Alternative embodiments could use a different time constant, a higher order filter, a finite-impulse response (FIR) filter, a non-linear filtering (for example a median filter). The function of baseline removal is to produce the Relative Temperature signal 603, a signal that represents a displacement from a slowly varying baseline. In certain embodiments, the baseline is estimated by the LPF 303 and baseline removal is performed by the subtraction operation 304. Alternative embodiments may use a different time constant in the low pass filter, a FIR filter, or a higher order filter. In some situations, the baseline may not change significantly during exercise, and therefore the relative signal will not change notably. Certain embodiments may limit the rate of change of the baseline filter output in addition to the low pass filter. In certain alternative embodiments, the logic 120, one or more processors or other circuits within the pacemaker, detects when exercise is occurring to hold the value of the baseline. Alternatively or additionally, the baseline can be adjusted on a daily basis in order to synchronize with the patient's daily temperature pattern.

The Dip Response 604 is configured to manage a rapid initial increase in a target heart rate of the pacemaker at the onset of exercise, namely when the patient is in an exercise onset state. The Dip Response 604 may be implemented by the logic 120, one or more processors or other circuitry within the pacemaker to analyze the relative temperature signal 903 to determine the temperature within the blood. A sudden drop in temperature that can occur at the start of exercise. As one example, the Dip Response 604 may be implemented as all or a portion of the comparator 341, the switch 342, and the integrator 343 in FIG. 3. Another embodiment is to use a term that is proportional to the dip followed by a non-linear predefined function e.g. an inverting limiter, followed by an optional filter, e.g. a bandpass filter. Various combinations of the above described embodiments are also within the scope of the embodiments described herein. Alternative embodiments could replace these elements with alternative elements that behave similarly. Exemplary implementations of the integrator 343 were discussed above.

The Slope Response 606 is configured to manage a rate of change in the target heart rate while the blood temperature is increasing, where the rate of change is dependent on the rate of increase in the blood temperature. Physiologically, the blood temperature rises due to the release of heat during exercise. The rate of change in the blood temperature may be indicative of the nature of the exercise and consequently an appropriate rate of change in the heart rate. In certain embodiments, the Slope Response signal 607 is generated by the HPF 321, followed by the rectifier 322 and multiplier 323, as shown in FIG. 3. As noted above, a BPF can be used in place of the HPF 321, in which case it is also possible that a combination of a LPF and a HPF can be used to implement such a BPF. Alternative embodiments could determine a slope based on sample points of the relative temperature signal 351, or in other manners.

The Proportional Response 608 is configured to provide a rate increase from the temperature rise due to sustained exercise. In an embodiment, the Proportional Response signal 909 is generated by determining a moving baseline temperature signal 352 and subtracting the moving baseline temperature signal 352 from the relative temperature signal 351. Other variations are also possible and are within the scope of the embodiments described herein.

The Combiner 611 is configured to combine the Dip Response signal 605, Slope Response signal 607, Proportional Response signal 609, and the Base Rate 610 into a single Combined Response signal 612. In an embodiment, only one of the Dip Response signal 605 and the Slope Response signal 607 is combined with the Proportional Response and the Base Rate to produce the combined response signal 612, or more generally, the Sensor Indicated Rate signal 616. For example, only the larger of the Dip Response signal 605 and the Slope Response signal 607 can be used, or just a predetermined one of the two can be used.

The Value Limiter 613 is configured to limit the combined response 612 to remain within a selected range, thereby limiting the Sensor Indicated Rate to values within a select range. In an embodiment, with reference to FIG. 3, the upper limit of the selected range is enforced by the Limiter block 326. A lower limit is not required because the prior computations are configured to avoid producing a value below the Base Rate.

The Rate-of-change Limiter 615 is configured to limit the rate of change of the target pacing rate. In an embodiment, with reference to FIG. 3, limiting the rate of change in the target pacing rate may be performed by the slew rate limiter 328, which can be implemented, e.g., using a low pass filter, but is not limited thereto. A step change to the input to such a low pass filter results in an output change with limited slope that decreases exponentially. In certain embodiments, the time constant is the same for positive and negative changes. In an alternative embodiment, different time constants may be applied for each direction. In yet another alternative embodiment, a slew limiter may be utilized instead of a low pass filter, which would limit the change (difference) of the next output value to be no more than a limiting value from the output value. A variation of this embodiment could impose different limits for decreasing and increasing changes. Moreover, the limiting values could vary depending on the current rate.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

FIGS. 1A and 1B, which were discussed above, where used to describe an exemplary leadless pacemaker in which embodiments of the present technology can be implanted. Embodiments of the present technology can be implemented within other types of implantable medical devices (IMDSs), or more generally, within other types of implantable medical systems, such as those described below with reference to FIGS. 7, 8, and 9, but are not limited thereto.

Figure 7:
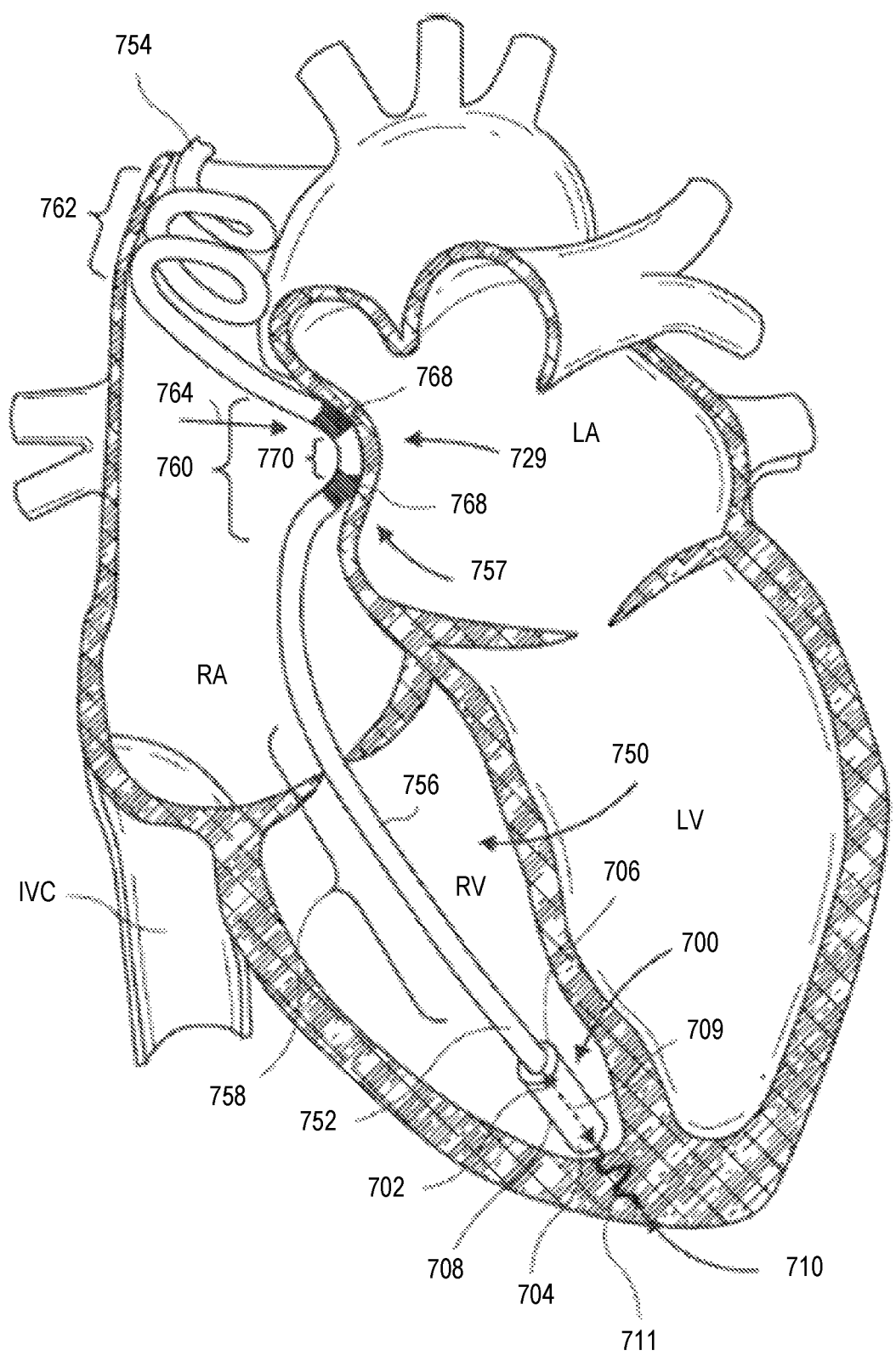
FIG. 7 is a simplified diagram of an embodiment of intra-cardiac medical device (ICMD).

FIG. 7 illustrates an intra-cardiac medical device (ICMD) 700 formed in accordance with embodiments herein. The ICMD 700 has been placed through the superior vena cava, through the right atrium and into the right ventricle of the heart. Optionally, the ICMD 700 may have been introduced through the inferior vena cava. As another option, the ICMD 700 may be introduced into the left atrium through the intra-atrial septum, into the left ventricle through the intra-ventricular septum, into the left ventricle through the aorta, and the like. The atrial septum divides the two atria, while the tricuspid valve is shown between the right atrium and right ventricle. FIG. 7 also illustrates the right atrial appendage 729. The reader will appreciate that the view of FIG. 7 is simplified and somewhat schematic, but that nevertheless FIG. 7 and the other views included herein will suffice to illustrate adequately the placement and operation of certain embodiments. The term "septum" shall be used throughout to generally refer to any portion of the heart separating two chambers (e.g. RA to LA, RA to RV, RV to LV, LA to LV, RA to LV). The ICMD 700 is formed in accordance with an embodiment and may represent a pacemaker that functions in a DDD-mode, a cardiac resynchronization device, a cardioverter, a defibrillator and the like. When in DDD-mode, the ICMD 700 may sense in two chambers, pace in two chambers and inhibit pacing in either chamber based on intrinsic events sensed in that chamber or in the other chamber. The ICMD 700 is configured to be implanted entirely within a single local chamber of the heart. For example, the ICMD 700 may be implanted entirely and solely within the right atrium or entirely and solely within the right ventricle. Optionally, the ICMD 700 may be implanted entirely and solely within the left atrium or left ventricle through more invasive implant methods.

For convenience, hereafter the chamber in which the ICMD 700 is implanted shall be referred to as the "local" chamber. The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The ICMD 700 includes a housing 702 that includes a base 704 and a top end 706. The housing 702 extends along a longitudinal axis 709 between the base 704 and the top end 706. The housing 702 is elongated and tubular in shape and extends along the longitudinal axis 709. The base 704 is configured to be secured to the local chamber. In the example of FIG. 7, the base 704 is secured to the right ventricle. Optionally, the ICMD 700 may be located in, and the base 704 secured to the wall of the left ventricle, left atrium or right atrium.

The base 704 includes an active fixation member 710 provided thereon and extending outward from the base 704 in a direction generally along the longitudinal axis 709. A first electrode 711 (also referred to as an active electrode area) is provided on the active fixation member 710. In alternative embodiments, the first electrode 711 may be located adjacent to, but not on, the active fixation member. U.S. Pat. No. 9,242,102 describes a fixation mechanism separate from the pacing electrode and disposed on the distal portion of the housing that may be used in accordance with certain embodiments. The electrode 711 is provided at a first position such that, when the ICMD 700 is implanted in the local chamber, the first electrode 711 engages the local wall tissue at a local activation site within the conduction network of the local chamber (e.g., within the ventricular wall tissue at the apex of the right ventricle).

An intra-cardiac (IC) device extension 750 has a proximal end 752, a distal end 754 and an extension body 756 extending there between. The term "infra-cardiac" is used to indicate that the IC device extension 750 "generally" remains within the heart and associated vessels, such as the SVC, IVC, CS, pulmonary arteries and the like. The term "device" is used to indicate that the IC device extension 750 is an extension of the ICMD 700. The proximal end 752 is permanently or removably (through a header style connector) coupled to the housing 702 and located in the local chamber. A stabilization arm, may be provided on the distal end 752 of the extension body 756. A right atrial appendage (RAA) fixation mechanism, generally denoted at 757, is provided at an intermediate point along the length of the extension body 756 and aligned with the RAA 729. Optionally, the stabilization arm may be removed entirely and the extension body 756 may terminate near the RAA 729.

The temperature sensor and circuitry to analyze temperatures, as described in connection with FIGS. 1-6, may be provided in the housing 702 and/or in the IC device extension 750.

In the example of FIG. 7, the extension body 756 including a chamber transition sub-segment 758, an active interim-segment 760 and a stabilizer end-segment 762. The stabilization end-segment 762 is one exemplary structural implementation of the stabilization arm. The RAA fixation mechanism 757 is one exemplary structural implementation of an active interim-segment 760. The chamber transition sub-segment 758 is sufficient in length to extend from the local chamber (e.g., the right ventricle) through the tricuspid valve into an adjacent chamber (e.g., the right atrium). The chamber transition sub-segment 758 extends upward out of the right ventricle in a direction that generally follows the longitudinal axis 709.

The extension body 756 is formed of a biocompatible insulated material such as EFTE, silicon, OPTIM and the like. In general, the extension body 756 is formed of materials that are flexible yet exhibit a desired degree of shape memory such that once implanted, the active interim-segment 760 and stabilizer end-segment 762 are biased to return to a pre-formed shape. One or more insulated conductive wires are held within the extension body 756 and span from the ICMD 700 to any sensors or electrodes provided on the extension body 756.

The stabilizer end-segment 762 is located at the distal end 754 and in a pre-formed shape that is biased to extend slightly outward in a lateral direction (generally denoted at 764) relative to a length of the chamber in which the stabilizer end-segment 762 is located. The stabilizer end-segment 762 engages a first region of the heart. For example, the stabilizer end-segment 762 may extend upward into and engage the SVC. Optionally, the stabilizer end-segment 762 may extend downward into and engage the IVC. Optionally, the stabilizer end segment 762 may extend into the coronary sinus, pulmonary artery and the like.

The stabilizer end-segment 762 is pre-formed into a predetermined shape based upon which portion of the chamber is to be engaged. The flexible stabilizer end-segment 762 may be wrapped into at least one turn having a pre-formed diameter. For example, when intended to securely engage the SVC, the stabilizer end-segment 762 may be formed into a spiral shape with one or more windings or turns that are pre-disposed or biased to radially expand to a diameter sufficient to firmly fit against the interior walls of the SVC.

Optionally, the stabilizer end-segment 762 may utilize alternative shapes for SVC stabilization, such as an S-shape, a T-shape, a Y-shape, a U-shape and the like. Optionally, the stabilizer end-segment 762 may be split into multiple (e.g., 2-4) stabilizer end-segments that project outward in different directions and contact different areas of the wall tissue. A conductor wire extends within the extension body 756 from the ICMD 700 to the second electrode, and the conductor terminates at the second electrode such that the stabilizer end segment 762 is void of electrodes and conductor wires. When the stabilizer end-segment 762 lacks any sensors or electrodes, the stabilizer end-segment 762 will also lack any internal conductive wires.

Optionally, the stabilizer end-segment 762 may include one or more conductors, spanning from the distal end 754 to the ICMD 700, to be coupled to a programmer during implantation to provide communications, power, remote access to electrodes and the like.

The active interim-segment 760 includes one or more electrodes 768 that are provided thereon and in a trough area 774 of the C-shape or U-shape. The electrodes 768 are spaced apart from one another, within the trough area 774, by an inter-electrode spacing 770. For example, the second electrodes 768 may be biased to engage wall tissue in the right atrial appendage 729. The second electrodes 768 engage distal wall tissue at a distal activation site (relative to the chamber which the ICMD 700 is implanted) within the conduction tissue of the adjacent chamber. Optionally, tines or other active fixation members may be included around the hump or trough portion of the active interim-segment 760 in order to improve fixation as the RAA fixation mechanism.

As discussed below, a controller is provided within the housing 702 to cause stimulus pulses to be delivered, in a dual chamber synchronous manner, through the first and second electrodes 711, 768 to the local and distal activation sites, respectively. The stimulus pulses delivered at the distal activation site are timed to cause contraction of the adjacent chamber in a predetermined relation to contraction of the local chamber. For example, the ICMD 700 may be configured to control delivery of the stimulus pulses from the first and second electrodes 711, 768 in accordance with a DDD pacing mode to a right atrium and right ventricle, while the ICMD is entirely located in one of the right atrium and right ventricle. For example, the controller may be configured to control delivery of the stimulus pulses from the first and second electrodes 711, 768 in accordance with a DDD pacing mode to a left atrium and left ventricle, while the ICMD is entirely located in one of the left atrium and left ventricle.

Figure 8:
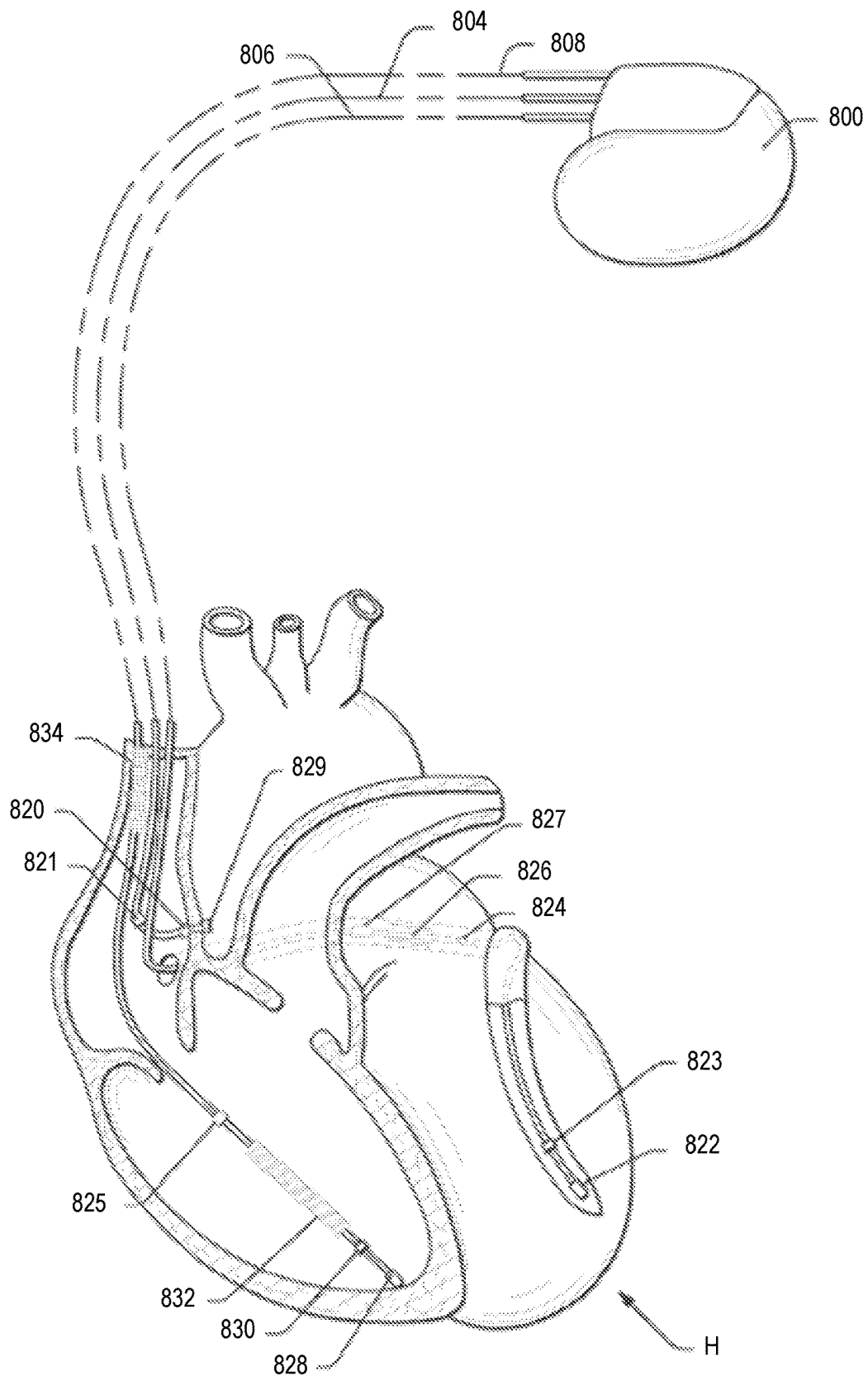
FIG. 8 is a simplified diagram of an embodiment of an implantable stimulation device in electrical communication with one or more leads implanted in a patient's heart for sensing conditions in the patient, delivering therapy to the patient, or providing some combination thereof.

FIG. 8 illustrates a cardiac pacemaker and/or implantable cardioverter-defibrillator (ICD) that utilizes one or more electrically-conductive leads that traverses blood vessels and heart chambers in order to connect a canister with electronics and a power source (the can) to electrodes affixed to the heart for the purpose of electrically exciting cardiac tissue and measuring myocardial electrical activity formed in accordance with embodiments herein. In certain alternative embodiments, a subcutaneous ICD that does not use endocardial, transvenous, or epicardial lead wires and can deliver defibrillation using subcutaneous electrodes formed in accordance with embodiments herein. For a more detailed description of a subcutaneous ICD, the reader is directed to U.S. Pat. No. 7,925,343, "Subcutaneous implantable cardiac device system with low defibrillation thresholds and improved sensing" (Min), which is incorporated herein by reference.

In FIG. 8 temperature sensing may be performed in conjunction with an implantable cardiac device (e.g., a stimulation device such as an implantable cardioverter defibrillator, a pacemaker, etc.). Here, one or more of the operations described above may be implemented in or in conjunction with such an implantable cardiac device. It should be appreciated that this example is provided for explanatory purposes and that temperature sensing may be implemented using other types of devices.

FIG. 8 illustrates an implantable cardiac device 800 in electrical communication with a patient's heart H by way of three leads 804, 806, and 808, suitable for delivering multi-chamber stimulation and shock therapy. To sense atrial cardiac signals and to provide right atrial chamber stimulation therapy, the device 800 is coupled to an implantable right atrial lead 804 having, for example, an atrial tip electrode 820, which typically is implanted in the patient's right atrial appendage or septum. FIG. 8 also shows the right atrial lead 804 as having an optional atrial ring electrode 821.

To sense left atrial and ventricular cardiac signals and to provide left chamber pacing therapy, device 800 is coupled to a coronary sinus lead 806 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 806 is designed to receive atrial and ventricular cardiac signals and to deliver left ventricular pacing therapy using, for example, a left ventricular tip electrode 822 and, optionally, a left ventricular ring electrode 823; provide left atrial pacing therapy using, for example, a left atrial ring electrode 824; and provide shocking therapy using, for example, a left atrial coil electrode 826 (or other electrode capable of delivering a shock). For a more detailed description of a coronary sinus lead, the reader is directed to U.S. Pat. No. 5,466,254, "Coronary Sinus Lead with Atrial Sensing Capability".

The device 800 is also shown in electrical communication with the patient's heart H by way of an implantable right ventricular lead 808 having, in this implementation, a right ventricular tip electrode 828, a right ventricular ring electrode 830, a right ventricular (RV) coil electrode 832 (or other electrode capable of delivering a shock), and a superior vena cava (SVC) coil electrode 834 (or other electrode capable of delivering a shock). Typically, the right ventricular lead 808 is transvenously inserted into the heart H to place the right ventricular tip electrode 828 in the right ventricular apex so that the RV coil electrode 832 will be positioned in the right ventricle and the SVC coil electrode 834 will be positioned in the superior vena cava. Accordingly, the right ventricular lead 808 is capable of sensing or receiving cardiac signals, and delivering stimulation in the form of pacing and shock therapy to the right ventricle.

Any of the leads 804, 806, and 808 may include one or more temperature sensors as taught herein. Temperature signals generated by a temperature sensor may be transmitted to the device 800 via one or more conductors that run through a corresponding cardiac lead. The device 800 may then utilize the corresponding temperature readings to commence or alter therapy for the patient, or to forward the temperature information or sensor indicated rate response or other programming information to an external device, such as a leadless pacemaker or a programmer external to the patient.

In certain embodiments, conductors associated with other components of the lead 808 (e.g., electrodes 828, 830, and 832) may be routed through the passageway(s) in the bottom portion of the sensor assembly.

It should be appreciated that temperature may be measured in various chambers of the heart or related vessels and that other mechanisms may be employed to measure temperature in a given chamber or vessel.

The device 800 may connect to leads other than those specifically shown. In addition, the leads connected to the device 800 may include components other than those specifically shown. For example, a lead may include other types of electrodes, sensors or devices that serve to otherwise interact with a patient or the surroundings.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, implemented as discrete wires, or in other ways.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Figure 9:
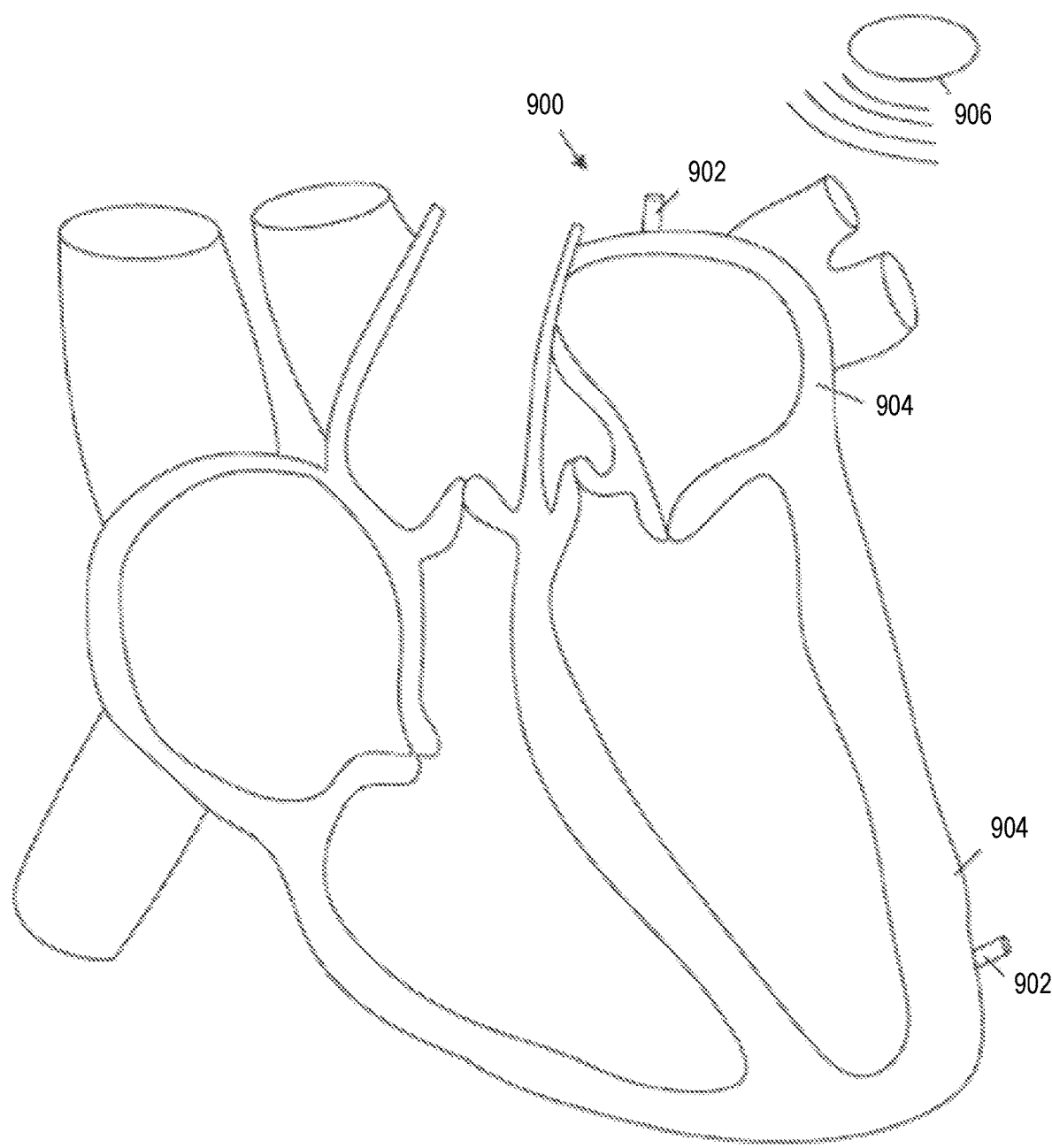
FIG. 9 is a simplified diagram illustrating an example of a cardiac rhythm management system formed in accordance with certain embodiments herein.

Referring to FIG. 9, a pictorial diagram shows an embodiment of a cardiac pacing system 900 including one or more leadless cardiac pacemakers 902 with conducted communication for performing cardiac pacing in conjunction with an implantable cardioverter-defibrillator (ICD) 906. The system 900 can implement for example single-chamber pacing, dual-chamber pacing, or three-chamber pacing for cardiac resynchronization therapy, without requiring pacing lead connections to the defibrillator 906. The illustrative cardiac pacing system 900 comprises at least one leadless cardiac pacemaker 902 configured for implantation in electrical contact with a cardiac chamber 904 and configured to perform cardiac pacing functions in combination with a co-implanted implantable cardioverter-defibrillator (ICD) 906. One or more of the leadless cardiac pacemakers 902 can comprise at least two leadless electrodes 908 configured for delivering cardiac pacing pulses, sensing evoked and/or natural cardiac electrical signals, and uni-directionally or bi-directionally communicating with the co-implanted ICD 906.

According to certain embodiments, a temperature sensor may be provided in the housing or integrally attached to the housing of one or more of the leadless pacemakers 902 and circuitry to analyze temperature signals generated by the temperature sensor may be provided in the housing of the ICD 906, which may be a subcutaneous ICD. According to certain embodiments, circuitry to analyze temperatures may be provided in the housing of one of the leadless pacemakers 902 and the temperature sensor may be located in the other leadless pacemakers 902. Other variations of the placement of the temperature sensors and circuitry to analyze the temperature, given the disclosure herein, will be understood by one of skill in the art.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements. In addition, terminology of the form "at least one of A, B, or C" or "one or more of A, B, or C" or "at least one of the group consisting of A, B, and C" used in the description or the claims means "A or B or C or any combination of these elements." For example, this terminology may include A, or B, or C, or A and B, or A and C, or A and B and C, or 2A, or 2B, or 2C, and so on.

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above, it will be understood that the teachings herein are intended to cover any changes, adaptations or modifications that are within the scope of the disclosure.

The blocks, modules, and controllers described herein may be implemented in various manners, such as through one or more of dedicated hardware, circuitry (integrated or discrete), firmware and/or microprocessor based architectures. One or more of the blocks, modules, and controllers described herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the (module/controller) represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The blocks, modules, and controllers may execute a set of instructions that are stored in one or more storage elements, in order to process data. The storage elements may also store data or other information as desired or needed. The storage element may be in the form of an information source or a physical memory element within the blocks, modules, and controllers. The set of instructions may include various commands that instruct the (module/controller) to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless defined otherwise, all technical terms used herein have the same meanings as commonly understood by one of ordinary skill in the art of cardiac technologies. Specific methods, devices, and materials may be described in this application, but any methods and materials similar or equivalent to those described herein can be used in the practice of the present technology. While embodiments of the present technology have been described in some detail and by way of exemplary illustrations, such illustration is for purposes of clarity of understanding only, and is not intended to be limiting. Various terms have been used in the description to convey an understanding of the present technology; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the present technology is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the present technology, the claims to the present technology are not bound by such theory. Moreover, any one or more features of any embodiment of the present technology can be combined with any one or more other features of any other embodiment of the present technology, without departing from the scope of the present technology. Still further, it should be understood that the present technology is not limited to the embodiments that have been set forth for purposes of exemplification, but is to be defined only by a fair reading of claims that are appended to the patent application, including the full range of equivalency to which each element thereof is entitled.

It should be appreciated from the above that the various structures and functions described herein may be incorporated into a variety of apparatuses (e.g., a lead, a monitoring device, a stimulation device, etc.) and implemented in a variety of ways. Different embodiments of the biostimulator may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may simply send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, implemented as discrete wires, or in other ways.

The recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

What is claimed is:

1. For use with an implantable medical system, a method for providing a temperature based rate response for a patient within which the implantable medical system is implanted, the method comprising:
sensing a blood temperature signal indicative of a core body temperature of the patient within which the implantable medical system is implanted;
producing a relative temperature signal based on the blood temperature signal;

producing a moving baseline temperature signal based on the relative temperature signal such that the moving baseline temperature signal follows the relative temperature signal during an initial drop in the blood temperature signal that occurs during an onset of activity, and the moving baseline temperature signal decays towards zero during an upswing in the blood temperature signal that follows the initial drop in the blood temperature signal;

producing a proportional response signal based on the relative temperature signal and the moving baseline temperature signal;

producing a sensor indicated rate response signal based on the proportional response signal and a base rate; and controlling a pacing rate of the implantable medical system based on the sensor indicated rate response signal.

2. The method of claim 1, wherein the producing the proportional response signal based on the relative temperature signal and the moving baseline temperature signal comprises:

subtracting the moving baseline temperature signal from the relative temperature signal to produce a difference signal indicative of a difference between the relative temperature signal and the moving baseline temperature signal; and producing the proportional response signal based on positive portions of the difference signal.

3. The method of claim 2, wherein the producing the proportional response signal based on positive portions of the difference signal comprises:

multiplying positive portions of the difference signal by a proportional gain value to thereby produce the proportional response signal; or applying a predetermined function to positive portions of the difference signal to thereby produce the proportional response signal.

4. The method of claim 1, wherein:

the proportional response signal provides for an increase in the pacing rate, based on a difference between the relative temperature signal and the moving baseline temperature signal, during an upswing in the blood temperature signal that follows an initial drop in the blood temperature signal that occurs during an onset of activity; and the proportional response signal provides for a decrease in the pacing rate, based on the difference between the relative temperature signal and the moving baseline temperature signal, during a downswing in the blood temperature signal that occurs in response to a reduction or cessation in activity.

5. The method of claim 1, further comprising:

producing at least one of a dip response signal or a slope response signal; and wherein the producing the sensor indicated rate response signal is also based on at least one of the dip response signal or the slope response signal;

wherein the dip response signal provides for an increase in the pacing rate during an initial drop in the blood temperature signal that occurs during an onset of activity; and wherein the slope response signal provides for an increase in the pacing rate, based on a slope of the relative temperature signal, during an upswing in the blood temperature signal that follows an initial drop in the blood temperature signal.

6. The method of claim 5, wherein:

the producing at least one of the dip response signal or the slope response signal comprises producing both the dip response signal and the slope response signal; and the producing the sensor indicated rate response signal comprises producing the sensor indicated rate response signal based on a combination of the proportional response signal, the dip response signal, the slope response signal, and the base rate.

7. The method of claim 6, wherein:

the producing the sensor indicated rate response signal based on the combination of the proportional response signal, the dip response signal, the slope response signal, and the base rate comprises producing the sensor indicated rate response signal by summing the proportional response signal, the dip response signal, the slope response signal, and the base rate.

8. The method of claim 6, wherein the producing the dip response signal comprises:

comparing the relative temperature signal to a dip threshold;

providing a dip onset rate value to an input of an integrator while the relative temperature signal is less than the dip threshold;

providing a dip decay rate value to the input of the integrator while the relative temperature signal is greater than the dip threshold; and using positive portions of a signal output by the integrator as the dip response signal.

9. The method of claim 6, wherein the producing the slope response signal comprises:

producing a signal indicative of a positive slope of the relative temperature signal; and either multiplying the signal indicative of the positive slope of the relative temperature signal by a slope gain value to thereby produce the slope response signal, or applying a predetermined function to the signal indicative of the positive slope of the relative temperature signal to thereby produce the slope response signal.

10. The method of claim 9, wherein the producing the signal indicative of the positive slope of the relative temperature signal comprises:

providing the relative temperature signal to a high pass filter (HPF) to thereby produce a signal indicative of a slope of the relative temperature signal, and providing an output of the HPF to a rectifier to thereby produce the signal indicative of the positive slope of the relative temperature signal; or determining a difference between two temporally different samples of the relative temperature signal, and producing the signal indicative of the positive slope of the relative temperature signal based on the difference.

11. The method of claim 1, wherein the producing the relative temperature signal based on the blood temperature signal comprises:

producing a short term average (STA) of the blood temperature signal;

producing a long term average (LTA) of the blood temperature signal; and producing the relative temperature signal by subtracting the LTA of the blood temperature signal from the STA of the blood temperature signal.

12. The method of claim 1, wherein the producing the sensor indicated rate response signal comprises:

producing a rate adjustment signal based on the portion response signal;

adding the rate adjustment signal to a base rate to produce the sensor indicated rate response signal; and limiting at least one of a magnitude or a slew rate of the sensor indicated rate response signal.

13. An implantable medical system, comprising:
one or more pulse generators configured to selectively produce pacing pulses;
one or more electrodes configured to deliver pacing pulses produced by at least one of the one or more pulse generators to a heart of a patient within which the implantable medical system is implanted;
a temperature sensor configured to produce a blood temperature signal indicative of a core body temperature of the patient within which the implantable medical system is implanted; and
a controller configured to:
produce a relative temperature signal based on the blood temperature signal;
produce a moving baseline temperature signal based on the relative temperature signal, wherein the moving baseline temperature signal follows the relative temperature signal during an initial drop in the blood temperature signal that occurs during an onset of activity, and the moving baseline temperature signal decays towards zero during an upswing in the blood temperature signal that follows the initial drop in the blood temperature signal;
produce a proportional response signal based on the relative temperature signal and the moving baseline temperature signal;
produce a sensor indicated rate response signal based on the proportional response signal and a base rate; and
control delivery of the pacing pulses to thereby control a pacing rate based on the sensor indicated rate response signal.

14. The implantable medical system of claim 13, wherein the controller is configured to produce the proportional response signal based on the relative temperature signal and the moving baseline temperature signal by:
subtracting the moving baseline temperature signal from the relative temperature signal to produce a difference signal indicative of a difference between the relative temperature signal and the moving baseline temperature signal; and
producing the proportional response signal based on positive portions of the difference signal.

15. The implantable medical system of claim 13, wherein:
the proportional response signal provides for an increase in the pacing rate, based on a difference between the relative temperature signal and the moving baseline temperature signal, during an upswing in the blood temperature signal that follows an initial drop in the blood temperature signal that occurs during an onset of activity; and
the proportional response signal provides for a decrease in the pacing rate, based on the difference between the relative temperature signal and the moving baseline temperature signal, during a downswing in the blood temperature signal that occurs in response to a reduction or cessation in activity.

16. The implantable medical system of claim 13, wherein the controller is also configured to:
produce at least one of a dip response signal or a slope response signal; and
produce the sensor indicated rate response signal also based on at least one of the dip response signal or the slope response signal;
wherein the dip response signal provides for an increase in the pacing rate during an initial drop in the blood temperature signal that occurs during an onset of activity; and
wherein the slope response signal provides for an increase in the pacing rate, based on a slope of the relative temperature signal, during an upswing in the blood temperature signal that follows an initial drop in the blood temperature signal.

17. The implantable medical system of claim 16, wherein the controller is configured to:
produce both the dip response signal and the slope response signal; and
produce the sensor indicated rate response signal based on a combination of the proportional response signal, the dip response signal, the slope response signal, and the base rate.

18. The implantable medical system of claim 17, wherein the controller is configured to:
compare the relative temperature signal to a dip threshold;
provide a dip onset rate value to an input of an integrator while the relative temperature signal is less than the dip threshold;
provide a dip decay rate value to the input of the integrator while the relative temperature signal is greater than the dip threshold; and
use positive portions of a signal output by the integrator as the dip response signal.

19. The implantable medical system of claim 17, wherein the controller is configured to add the proportional response signal, the dip response signal, the slope response signal, and the base rate to produce the sensor indicated rate response signal, and limit at least one of a magnitude or a slew rate of the sensor indicated rate response signal.

20. The implantable medical system of claim 13, wherein the controller is configured to:
produce a short term average (STA) of the blood temperature signal;
produce a long term average (LTA) of the blood temperature signal; and
produce the relative temperature signal by subtracting the LTA of the blood temperature signal from the STA of the blood temperature signal.

21. For use with an implantable medical system, a method for providing a temperature based rate response for a patient within which the implantable medical system is implanted, the method comprising:
sensing a blood temperature signal indicative of a core body temperature of the patient within which the implantable medical system is implanted;
producing a relative temperature signal based on the blood temperature signal;
producing a moving baseline temperature signal based on the relative temperature signal;
producing a proportional response signal based on the relative temperature signal and the moving baseline temperature signal;
producing a dip response signal and a slope response signal based on the relative temperature signal;
producing a sensor indicated rate response signal based on a sum of the proportional response signal, the dip response signal, and the slope response signal; and controlling a pacing rate of the implantable medical system based on the sensor indicated rate response signal.

22. The method of claim 21, wherein:
the dip response signal provides for an increase in the pacing rate during an initial drop in the blood temperature signal that occurs during an onset of activity;
the slope response signal provides for an increase in the pacing rate, based on a slope of the relative temperature signal, during an upswing in the blood temperature signal that follows the initial drop in the blood temperature signal;
the proportional response signal provides for an increase in the pacing rate, based on a difference between the relative temperature signal and the moving baseline temperature signal, during an upswing in the blood temperature signal that follows the initial drop in the blood temperature signal that occurs during the onset of activity; and
the proportional response signal provides for a decrease in the pacing rate, based on the difference between the relative temperature signal and the moving baseline temperature signal, during a downswing in the blood temperature signal that occurs in response to a reduction or cessation in activity.

23. The method of claim 21, wherein the moving baseline temperature signal is produced based on the relative temperature signal such that the moving baseline temperature signal follows the relative temperature signal during an initial drop in the blood temperature signal that occurs during an onset of activity, and the moving baseline temperature signal decays towards zero during an upswing in the blood temperature signal that follows the initial drop in the blood temperature signal.

24. The method of claim 21, wherein the producing the sensor indicated rate response is signal is based on the sum of the proportional response signal, the dip response signal, and the slope response signal, also summed with a base rate.

* * * * *